United States Patent
Futamura et al.

(10) Patent No.: US 9,266,870 B2
(45) Date of Patent: Feb. 23, 2016

(54) HETEROAROMATIC METHYL CYCLIC AMINE DERIVATIVE

(71) Applicant: TAISHO PHARMACEUTICAL CO., LTD., Toshima-ku, Tokyo (JP)

(72) Inventors: Aya Futamura, Tokyo (JP); Yuko Araki, Tokyo (JP); Masahito Abe, Tokyo (JP); Hiroshi Ohta, Tokyo (JP); Ryo Suzuki, Tokyo (JP); Dai Nozawa, Tokyo (JP)

(73) Assignee: TAISHO PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 14/407,353

(22) PCT Filed: Jun. 13, 2013

(86) PCT No.: PCT/JP2013/066322
§ 371 (c)(1),
(2) Date: Dec. 11, 2014

(87) PCT Pub. No.: WO2013/187467
PCT Pub. Date: Dec. 19, 2013

(65) Prior Publication Data
US 2015/0183768 A1 Jul. 2, 2015

(30) Foreign Application Priority Data
Jun. 15, 2012 (JP) .................................. 2012-135277

(51) Int. Cl.
| | |
|---|---|
| A61K 31/506 | (2006.01) |
| C07D 413/14 | (2006.01) |
| C07D 405/14 | (2006.01) |
| C07D 401/14 | (2006.01) |
| A61K 31/4439 | (2006.01) |
| A61K 31/4192 | (2006.01) |
| C07D 403/12 | (2006.01) |
| A61K 31/5355 | (2006.01) |

(52) U.S. Cl.
CPC .................................. *C07D 413/14* (2013.01)

(58) Field of Classification Search
CPC ............ A61K 31/506; A61K 31/4439; A61K 31/4192; A61K 31/5355; C07D 413/14; C07D 405/14; C07D 401/14; C07D 403/12
USPC ............. 544/333; 548/131; 546/269.4, 275.4, 546/274.1, 272.1; 514/228.8
See application file for complete search history.

(56) References Cited

U.S. PATENT DOCUMENTS

| | | | |
|---|---|---|---|
| 2010/0063056 A1 | 3/2010 | Coleman et al. | |
| 2010/0197652 A1 | 8/2010 | Bergman et al. | |
| 2011/0201591 A1 | 8/2011 | Bergman et al. | |
| 2011/0207747 A1 | 8/2011 | Bergman et al. | |
| 2011/0212968 A1 | 9/2011 | Aissaoui et al. | |
| 2011/0312961 A1 | 12/2011 | Cox et al. | |

FOREIGN PATENT DOCUMENTS

| | | |
|---|---|---|
| JP | 2010-520206 A | 6/2010 |
| JP | 2010-535769 A | 11/2010 |
| JP | 2012-505263 A | 3/2012 |
| JP | 2012-506376 A | 3/2012 |
| JP | 2012-507538 A | 3/2012 |
| JP | 2012-507539 A | 3/2012 |
| WO | 03/002559 A2 | 1/2003 |
| WO | 2008/062878 A1 | 5/2008 |
| WO | 2008/108991 A1 | 9/2008 |
| WO | 2009/020642 A1 | 2/2009 |
| WO | 2010/044054 A1 | 4/2010 |
| WO | 2010/048013 A1 | 4/2010 |
| WO | WO 2010/038200 * | 4/2010 |
| WO | 2010/051236 A1 | 5/2010 |
| WO | 2010/051237 A1 | 5/2010 |
| WO | 2012/081692 A1 | 6/2012 |
| WO | 2012/153729 A1 | 11/2012 |

OTHER PUBLICATIONS

Hoever; Clinical Pharmacology and Therapeutics, 2012, 91, 975-985.*
Catherine Brisbare-Roch, et al., "Promotion of sleep by targeting the orexin system in rats, dogs and humans", Nature Medicine, Feb. 2007, pp. 150-155, vol. 13, No. 2.
Christopher D. Cox., "Discovery of the Dual Orexin Receptor Antagonist [(7R)-4-(5-Chloro-1,3-benzoxazol-2-yl)-7-methyl-1,4-diazepan-l-yl][5-methyl-2-(2H-1,2,3-triazol-2-yl)phenyl]methanone (MK-4305) for the Treatment of Insomnia", Journal of Medicinal Chemistry, 2010, pp. 5320-5332, vol. 53.
Jim J. Hagan, "Orexin A activates locus coeruleus cell firing and increases arousal in the rat", Proc. Natl. Acad. Sci., Sep. 1999, pp. 10911-10916, vol. 96.

(Continued)

*Primary Examiner* — Janet L Andres
*Assistant Examiner* — Daniel Carcanague
(74) *Attorney, Agent, or Firm* — Sughrue Mion, PLLC

(57) ABSTRACT

A heteroaromatic methyl cyclic amine derivative represented by formula (IA) or a pharmaceutically acceptable salt thereof is useful for treatment or prophylaxis of diseases such as sleep disorder, depression, anxiety disorder, panic disorder, schizophrenia, drug dependence, Alzheimer's disease, Parkinson's disease, Huntington's disease, eating disorder, cephalalgia, hemicrania, pain, digestive diseases, epilepsy, inflammation, immune-related diseases, endocrine-related diseases and hypertension, on the basis of an orexin (OX) receptor antagonist activity.

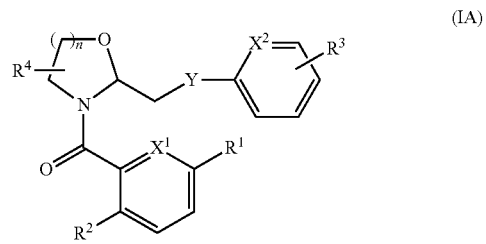

(IA)

9 Claims, No Drawings

(56) References Cited

OTHER PUBLICATIONS

John Gatfield, et al., "Orexin Receptor Antagonists: A New Concept in CNS Disorders?", ChemMedChem, 2010, pp. 1197-1214, vol. 5.

Jacob N. Marcus, et al., "Differential Expression of Orexin Receptors 1 and 2 in the Rat Brain", The Journal of Comparative Neurology, 2001, pp. 6-25, vol. 435.

Toshiaki Nakamura, et al., "Orexin-induced hyperlocomotion and stereotypy are mediated by the dopaminergic system", Brain Research, 2000, pp. 181-187, vol. 873.

M.I. Smith, et al., "Evidence implicating a role for orexin-1 receptor modulation of paradoxical sleep in the rat", Neuroscience Letters, 2003, pp. 256-258, vol. 341.

Prashant Trivedi, et al., "Distribution of orexin receptor mRNA in the rat brain", FEBS Letters, 1998, pp. 71-75, vol. 438.

Akihiro Yamanaka, et al., "Orexins Activate Histaminergic Neurons via the Orexin 2 Receptor", Biochemical and Biophysical Research Communications, 2002, pp. 1237-1245, vol. 290.

Jamie M. Zeitzer, et al., "The neurobiology of hypocretins (orexins), narcolepsy and related therapeutic interventions", Trends in Pharmacological Sciences, Jul. 2006, pp. 368-374, vol. 27, No. 7.

Yun Zhu, et al., "Orexin Receptor Type-1 Couples Exclusively to Pertussis Toxin-Insensitive G-Proteins, While Orexin Receptor Type-2 Couples to Both Pertussis Toxin-Sensitive and -Insensitive G-Proteins", Journal of Pharmacological Sciences, 2003, pp. 259-266, vol. 92.

International Search Report for PCT/JP2013/066322 dated Jul. 9, 2013 [PCT/ISA/210].

* cited by examiner

HETEROAROMATIC METHYL CYCLIC AMINE DERIVATIVE

CROSS REFERENCE TO RELATED APPLICATIONS

This application is a National Stage of International Application No. PCT/JP2013/066322, filed on Jun. 13, 2013, which claims priority from Japanese Patent Application No. 2012-135277, filed on Jun. 15, 2012, the contents of all of which are incorporated herein by reference in their entirety.

TECHNICAL FIELD

The present invention relates to a compound having an orexin (OX) receptor antagonistic activity and a pharmaceutically acceptable salt thereof, and a therapeutic or preventive drug for disease such as sleep disorder, depression, anxiety disorder, panic disorder, schizophrenia, drug dependence, Alzheimer's disease, Parkinson's disease, Huntington's disease, eating disorder, headache, migraine, pain, gastrointestinal disease, epilepsy, inflammation, immunological disease, endocrine diseases or hypertension, containing such a compound or salt as an active ingredient.

BACKGROUND ART

Orexin is a neuropeptide spliced from prepro-orexin, which is expressed specifically in the lateral hypothalamic area. Up to date, OX-A composed of 33 amino acids and OX-B composed of 28 amino acids have been identified, both of which are involved in the regulation of sleep-wake pattern and the regulation of feeding.

Both OX-A and OX-B act on OX receptors. Two subtypes, OX1 and OX2 receptors, of the OX receptors have been cloned so far, and both of which are known to be seven-transmembrane G protein-coupled receptors expressed mainly in the brain. OX1 receptor is coupled specifically with Gq among the G protein subclasses, whereas OX2 receptor is coupled with Gq and Gi/o (see Non Patent Literature 1 and Non Patent Literature 2). Ox receptor subtypes are selectively expressed in the brain, and OX1 receptor is expressed in high density in the locus coeruleus, which is the nuclei originis of noradrenergic neurons, whereas OX2 receptor is expressed in high density in the tuberomammillary nucleus, which is the nuclei originis of histaminergic neuron (see Non Patent Literature 3, Non Patent Literature 4 and Non Patent Literature 5). The expression of both OX1 receptor and OX2 receptor are found in the raphe nucleus, which is the nuclei originis of serotoninergic neuron, and in the ventral tegmental area, which is the nuclei originis of dopaminergic neuron (see Non Patent Literature 3). The orexin neurons project to the monoaminergic neuron system at the brain stem and the hypothalamus and have excitatory effects to these neurons, and further the expression of OX2 receptor is also found in the cholinergic neuron at the brain stem responsible for regulating REM sleep and have effects to the nucleus activities thereof (see Non Patent Literature 3 and Non Patent literature 4).

In recent years, OX1 and OX2 receptors are focused on the role of the sleep-wake regulation, and the usefulness of OX receptor antagonists have been studied. When OX-A is intracerebroventricularly administered to a rat, increased spontaneous locomotor activity (see Non Patent Literature 6 and Non Patent Literature 7), increased stereotyped behavior (see Non Patent Literature 7), increased time spent awake (see Non Patent Literature 6), and the like, were observed. Decreased REM sleep produced by OX-A administration is completely antagonized by the pretreatment of an OX receptor antagonist (see Non Patent Literature 8). Further, it is reported that locomotor activity is decreased, sleep latency is shortened, and amount of non-REM sleep and REM sleep are increased by administering an orally available OX1 and OX2 receptors antagonist (see Non Patent Literature 9 and Non Patent Literature 10). Patent Literature 1 discloses a heteroaromatic ring derivative as the compound having OX receptor antagonistic activities but does not disclose the compound having the heteroaromatic methyl cyclic amine skeleton as described in the present application. Also, compounds, for example, having various structures described in Non Patent Literature 11 are generally known as OX receptor antagonists but the compounds having the heteroaromatic methyl cyclic amine skeleton described in the present application are not disclosed.

CITATION LIST

Patent Literature

Patent Literature 1: WO2003/002559

Non Patent Literature

Non Patent Literature 1: Zhu Y et al., J. Pharmacol. Sci., 92, 259-266, 2003.
Non Patent Literature 2: Zeitzer J M et al., Trends Pharmacol. Sci., 27, 368-374, 2006.
Non Patent Literature 3: Marcus J N et al., J. Comp. Neurol, 435, 6-25, 2001.
Non Patent Literature 4: Trivedi J P et al., FEBS Lett, 438, 71-75, 1998.
Non Patent Literature 5: Yamanaka A et al., Biochem. Biophys. Res. Commun., 290, 1237-1245, 2002.
Non Patent Literature 6: Hagan J J et al., Proc. Natl. Acad. Sci. USA, 96, 10911-10916, 1999.
Non Patent Literature 7: Nakamura T et al., Brain Res., 873, 181-187, 2000.
Non Patent Literature 8: Smith M I et al., Neurosci. Lett., 341, 256-258, 2003.
Non Patent Literature 9: Brisbare-Roch C et al., Nat. Med., 13, 150-155, 2007.
Non Patent Literature 10: Cox C D et al., J. Med. Chem., 53, 5320-5332, 2010.
Non Patent Literature 11: John G et al., Chem Med Chem., 5, 1197-1214, 2010.

SUMMARY OF INVENTION

Technical Problem

An object of the present invention is to find a novel compound which has an OX receptor antagonistic activity and provide a therapeutic or preventive drug for disease such as sleep disorder, depression, anxiety disorder, panic disorder, schizophrenia, drug dependence, Alzheimer's disease, Parkinson's disease, Huntington's disease, eating disorder, headache, migraine, pain, gastrointestinal disease, epilepsy, inflammation, immunological disease, endocrine disease or hypertension. More specifically, the object of the present invention is to provide a novel compound which exhibits good pharmacokinetics and safety together with a good OX receptor antagonistic activity.

Solution to Problem

The present inventors extensively studied on novel skeleton compounds having an antagonistic activity against orexin receptors and found that certain heteroaromatic methyl cyclic amine derivatives represented by the following formulae have good OX receptor antagonistic activities, whereby the present invention was accomplished.

Hereinafter, the present invention is described in detail. The aspects of the present invention (hereinafter referred to as "compound of the present invention") are as follows.

(1) A compound represented by formula (IA):

[Formula 1]

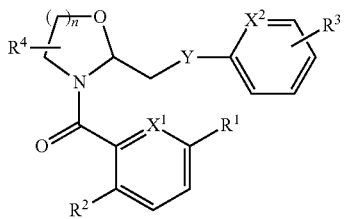

(IA)

wherein, $X^1$ and $X^2$ are the same or different and represent a nitrogen atom or formula CH;

Y represents any of the structures in the following formula group (a):

[Formula 2]

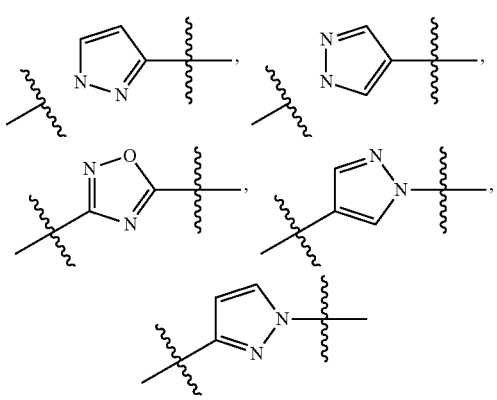

(a)

n represents 1 or 2;

$R^1$ represents a hydrogen atom, a halogen atom or a $C_{1-6}$ alkyl group;

$R^2$ represents a triazolyl group, a pyridyl group or a pyrimidinyl group;

$R^3$ represents a hydrogen atom, a halogen atom or a $C_{1-6}$ alkyl group, wherein the $C_{1-6}$ alkyl group may optionally be substituted with 1 to 3 halogen atoms; and $R^4$ represents a hydrogen atom or a $C_{1-6}$ alkyl group;

or a pharmaceutically acceptable salt thereof.

(2) The compound or a pharmaceutically acceptable salt thereof according to (1), wherein, in the above formula (IA), $R^2$ is a triazolyl group or a pyrimidinyl group; and $R^3$ is a halogen atom.

(3) The compound or a pharmaceutically acceptable salt thereof according to (1) or (2), wherein, in the above formula (IA), n is 2.

(4) A compound represented by formula (I):

[Formula 3]

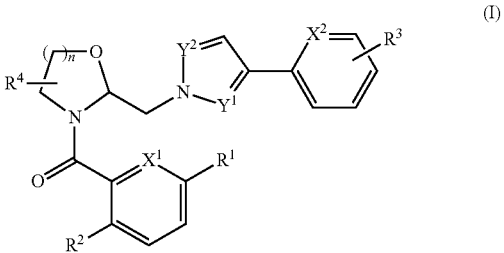

(I)

wherein, $X^1$ and $X^2$ are the same or different and represent a nitrogen atom or formula CH;

either one of $Y^1$ and $Y^2$ represents a nitrogen atom, and the other represents CH;

n represents 1 or 2;

$R^1$ represents a hydrogen atom, a halogen atom or a $C_{1-6}$ alkyl group;

$R^2$ represents a triazolyl group, a pyridyl group or a pyrimidinyl group;

$R^3$ represents a hydrogen atom, a halogen atom or a $C_{1-6}$ alkyl group, wherein the $C_{1-6}$ alkyl group may optionally be substituted with 1 to 3 halogen atoms; and $R^4$ represents a hydrogen atom or a $C_{1-6}$ alkyl group;

or a pharmaceutically acceptable salt thereof.

(5) The compound or a pharmaceutically acceptable salt thereof according to (4), wherein, in the above formula (I), $R^2$ is a triazolyl group or a pyrimidinyl group; and $R^3$ is a halogen atom.

(6) The compound or a pharmaceutically acceptable salt thereof according to (4) or (5), wherein, in the above formula (I), n is 2.

(7) The compound or a pharmaceutically acceptable salt thereof according to (1), which is a species or a mixture of two or more species selected from:

(−)-(2-{[3-(5-fluoropyridin-2-yl)-1H-pyrazol-1-yl]methyl}-1,3-oxazolidin-3-yl)[5-methyl-2-(2H-1,2,3-triazol-2-yl)phenyl]methanone, (−)-(2-{[4-(5-fluoropyridin-2-yl)-1H-pyrazol-1-yl]methyl}-1,3-oxazolidin-3-yl)[5-methyl-2-(2H-1,2,3-triazol-2-yl)phenyl]methanone, (−)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone, (−)-(2-{[4-(5-fluoropyridin-2-yl)-1H-pyrazol-1-yl]methyl}-1,3-oxazinan-3-yl)[5-methyl-2-(2H-1,2,3-triazol-2-yl)phenyl]methanone, (−)-[(2S,5S)-2-{[4-(5-fluoropyridin-2-yl)-1H-pyrazol-1-yl]methyl}-5-methyl-1,3-oxazolidin-3-yl][5-methyl-2-(2H-1,2,3-triazol-2-yl)phenyl]methanone, (−)-[(2S,5R)-2-{[4-(5-fluoropyridin-2-yl)-1H-pyrazol-1-yl]methyl}-5-methyl-1,3-oxazolidin-3-yl][5-methyl-2-(2H-1,2,3-triazol-2-yl)phenyl]methanone,

[(2S,4R)-2-{[3-(5-fluoropyridin-2-yl)-1H-pyrazol-1-yl]methyl}-4-methyl-1,3-oxazolidin-3-yl][5-methyl-2-(2H-1,2,3-triazol-2-yl)phenyl]methanone, (−)-(2S,4S)-2-{[3-(5-fluoropyridin-2-yl)-1H-pyrazol-1-yl]methyl}-4-methyl-1,3-oxazolidin-3-yl][5-methyl-2-(2H-1,2,3-triazol-2-yl)phenyl]methanone, (±)-2-{[3-(5-fluoropyridin-2-yl)-1H-pyrazol-1-yl]methyl}-1,3-oxazolidin-3-yl][5-methyl-2-(pyrimidin-2-yl)phenyl]methanone, (±)-(2-{[3-(5-fluoropyridin-2-yl)-1H-pyrazol-1-yl]methyl}-1,3-oxazolidin-3-yl)[5-fluoro-2-(pyrimidin-2-yl)phenyl]methanone, (±)-(2-{[3-(4-fluorophenyl)-1H-pyrazol-1-yl]methyl}-1,3-oxazolidin-3-yl)[5-methyl-2-(2H-1,2,3-triazol-2-yl)phenyl]methanone, (±)-(2-{[4-(4-fluorophenyl)-1H-pyrazol-1-yl]methyl}-1,3-oxazolidin-3-yl)[5-methyl-2-(2H-1,2,3-triazol-2-yl)phenyl]methanone, (±)-(2-{[4-(4-fluorophenyl)-1H-pyrazol-1-yl]methyl}-1,3-oxazolidin-3-yl)[5-methyl-2-(pyrimidin-2-yl)phenyl]methanone, (−)-(2-{[3-(4-fluorophenyl)-1H-pyrazol-1-yl]methyl}-1,3-oxazolidin-3-yl)[6-methyl-3-(2H-1,2,3-triazol-2-yl)pyridin-2-yl]methanone, (−)-(2-{[3-(4-fluorophenyl)-1H-pyrazol-1-yl]methyl}-1,3-oxazinan-3-yl)[6-methyl-3-(2H-1,2,3-triazol-2-yl)pyridin-2-yl]methanone, (−)-(2-{[3-(4-fluorophenyl)-1H-pyrazol-1-yl]methyl}-1,3-oxazinan-3-yl)[6-methyl-3-(pyrimidin-2-yl)pyridin-2-yl]methanone, (−)-(2-{[3-(5-fluoropyridin-2-yl)-1H-pyrazol-1-yl]methyl}-1,3-oxazinan-3-yl)[5-fluoro-2-(2H-1,2,3-triazol-2-yl)phenyl]methanone, (−)-(2-{[3-(5-fluoropyridin-2-yl)-1H-pyrazol-1-yl]methyl}-1,3-oxazinan-3-yl)[5-methyl-2-(pyrimidin-2-yl)phenyl]methanone, (−)-(2-{[4-(4-fluorophenyl)-1H-pyrazol-1-yl]methyl}-1,3-oxazinan-3-yl)[6-methyl-3-(2H-1,2,3-triazol-2-yl)pyridin-2-yl]methanone, (−)-(2-{[4-(4-fluorophenyl)-1H-pyrazol-1-yl]methyl}-1,3-oxazinan-3-yl)[6-methyl-3-(pyrimidin-2-yl)pyridin-2-yl]methanone, (−)-[2-{[3-(5-fluoropyridin-2-yl)-1H-pyrazol-1-yl]methyl}-1,3-oxazinan-3-yl][5-fluoro-2-(pyrimidin-2-yl)phenyl]methanone, (−)-[2-{[4-(4-fluorophenyl)-1H-pyrazol-1-yl]methyl}-1,3-oxazinan-3-yl][5-methyl-2-(2H-1,2,3-triazol-2-yl)phenyl]methanone, (−)-[2-{[5-(5-fluoropyridin-2-yl)-1,2,4-oxadiazol-3-yl]methyl}-1,3-oxazinan-3-yl][5-methyl-2-(2H-1,2,3-triazol-2-yl)phenyl]methanone, (−)-[2-{[5-(4-fluorophenyl)-1,2,4-oxadiazol-3-yl]methyl}-1,3-oxazinan-3-yl][5-methyl-2-(2H-1,2,3-triazol-2-yl)phenyl]methanone, (−)-[2-{[5-(4-fluorophenyl)-1,2,4-oxadiazol-3-yl]methyl}-1,3-oxazinan-3-yl][6-methyl-3-(2H-1,2,3-triazol-2-yl)pyridin-2-yl]methanone,

[(2S,4S)-2-{[4-(5-fluoropyridin-2-yl)-1H-pyrazol-1-yl]methyl}-4-methyl-1,3-oxazinan-3-yl][5-methyl-2-(2H-1,2,3-triazol-2-yl)phenyl]methanone, (−)-[(2S*,5S*)-2-{[4-(5-fluoropyridin-2-yl)-1H-pyrazol-1-yl]methyl}-5-methyl-1,3-oxazinan-3-yl][5-methyl-2-(2H-1,2,3-triazol-2-yl)phenyl]methanone, (−)-[2-{[3-(4-fluorophenyl)-1H-pyrazol-1-yl]methyl}-1,3-oxazinan-3-yl][5-methyl-2-(pyrimidin-2-yl)phenyl]methanone, (±)-[2-{[1-(5-fluoropyridin-2-yl)-1H-pyrazol-4-yl]methyl}-1,3-oxazinan-3-yl][5-methyl-2-(pyrimidin-2-yl)phenyl]methanone, (−)-[2-{[4-(4-fluorophenyl)-1H-pyrazol-1-yl]methyl}-1,3-oxazinan-3-yl][5-methyl-2-(pyrimidin-2-yl)phenyl]methanone, (−)-[2-{[1-(5-fluoropyridin-2-yl)-1H-pyrazol-4-yl]methyl}-1,3-oxazinan-3-yl][5-fluoro-2-(pyrimidin-2-yl)phenyl]methanone, (−)-[2-{[1-(5-fluoropyridin-2-yl)-1H-pyrazol-3-yl]methyl}-1,3-oxazolidin-3-yl][5-methyl-2-(2H-1,2,3-triazol-2-yl)phenyl]methanone, (−)-[2-{[1-(5-fluoropyridin-2-yl)-1H-pyrazol-4-yl]methyl}-1,3-oxazolidin-3-yl][5-methyl-2-(2H-1,2,3-triazol-2-yl)phenyl]methanone, (−)-[2-{[1-(5-fluoropyridin-2-yl)-1H-pyrazol-4-yl]methyl}-1,3-oxazinan-3-yl][5-methyl-2-(2H-1,2,3-triazol-2-yl)phenyl]methanone, and (−)-[(2S*,5R*)-2-{[4-(5-fluoropyridin-2-yl)-1H-pyrazol-1-yl]methyl}-5-methyl-1,3-oxazinan-3-yl][5-methyl-2-(2H-1,2,3-triazol-2-yl)phenyl]methanone.

(8) A pharmaceutical composition containing the compound or a pharmaceutically acceptable salt thereof according to any one of the above (1) to (7), as an active ingredient.

(9) A therapeutic or preventive drug for disease such as sleep disorder, depression, anxiety disorder, panic disorder, schizophrenia, drug dependence, Alzheimer's disease, Parkinson's disease, Huntington's disease, eating disorder, headache, migraine, pain, gastrointestinal disease, epilepsy, inflammation, immunological disease, endocrine disease or hypertension, containing the compound or a pharmaceutically acceptable salt thereof according to any one of the above (1) to (7), as an active ingredient.

Advantageous Effects of Invention

It is revealed that the heteroaromatic methyl cyclic amine derivative of the present invention shows an affinity to OX receptors and antagonistic activities against stimulation to the receptors by a physiological ligand.

DESCRIPTION OF EMBODIMENTS

The terms used in the present specification mean as follows.

The "halogen atom" refers to a fluorine atom, a chlorine atom, a bromine atom and an iodine atom.

The "$C_{1-6}$ alkyl group" means a linear or branched chain alkyl group having 1 to 6 carbon atoms and examples include groups such as methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl and neohexyl.

The "sleep disorder" used in the present specification refers to disorders at the disturbance of falling asleep, sleep, phase or awakening, where in including insomnia.

Further, the classification of insomnia includes disturbance of falling asleep, arousal during sleep, early-morning awakening and disturbance of deep sleep.

The "pharmaceutically acceptable salt" used in the present specification means a pharmaceutically acceptable acid addition salt and examples of the acid to be used include salts with an inorganic acid such as sulfuric acid, hydrochloric acid, hydrobromic acid, phosphoric acid and nitric acid; and salts with an organic acid such as acetic acid, benzoic acid, oxalic acid, lactic acid, malic acid, tartaric acid, fumaric acid, maleic acid, citric acid, malonic acid, mandelic acid, gluconic acid, galactaric acid, glucoheptonic acid, glycolic acid, glutamic acid, methanesulfonic acid, ethanesulfonic acid, benzenesulfonic acid, p-toluenesulfonic acid, camphor sulfonic acid and naphthalene-2-sulfonic acid. The conversion from a free compound to the above salt can be carried out by a conventional method.

Preferable embodiments of the compound of the present invention are described below.

Compounds, wherein $R^1$ is a halogen atom or a $C_{1-6}$ alkyl group, are preferable, with those wherein $R^1$ is a fluorine atom or a methyl group being more preferable, and with those wherein $R^1$ is a methyl group being further preferable.

Compounds, wherein $R^2$ is a triazolyl group or a pyrimidinyl group, are preferable, with those wherein $R^2$ is a 1,2,3-triazol-2-yl group or a pyrimidin-2-yl group being more preferable.

Compounds, wherein $R^3$ is a halogen atom, are preferable, with those wherein $R^3$ is a fluorine atom or a chlorine atom being more preferable, and with those wherein $R^3$ is a fluorine atom being further preferable.

Compounds, wherein $R^4$ is a hydrogen atom or a methyl group, are preferable.

Compounds, wherein n is 2, are preferable.

Additionally, when the compound of the present invention forms a hydrate or a solvate, they are also encompassed in the scope of the present invention. Similarly, pharmaceutically acceptable salts of the hydrates or solvates of the compound of the present invention are also encompassed in the scope of the present invention.

The compound of the present invention encompasses all of the enantiomers, diastereomers, equilibrium compounds, mixtures thereof in any ratio, racemic compounds, and the like.

The compound according to the present invention also includes those wherein at least one hydrogen atom, carbon atom, nitrogen atom, oxygen atom and halogen atom is substituted with a radioactive isotope or a stable isotope. These labelled compounds are useful for the studies on metabolism and pharmacokinetics and for biological analysis, or the like, as a receptor ligand, or the like.

The compound according to the present invention can be administered orally or parenterally. Dosage form thereof may be tablets, capsules, granules, powders, dusts, troches, ointments, creams, plasters, emulsions, suspensions, suppositories, injections, or the like, and any of which can be produced by a routine pharmaceutical preparation technique (for example, methods stipulated in The Japanese Pharmacopoeia Fifteenth Edition, or the like). These dosage forms can suitably be selected in accordance with patient's symptoms, age, body weight and purpose of treatment.

These pharmaceutical preparations can be produced by adding pharmacologically acceptable carriers, more specifically, excipients (for example, crystalline cellulose, starch, lactose, mannitol), binders (for example, hydroxypropylcellulose, polyvinylpyrrolidone), lubricants (for example, magnesium stearate, talc), disintegrators (for example, carboxymethyl cellulose calcium) and other pharmacologically acceptable various additives, to a composition containing the compound of the present invention.

The compound of the present invention can be orally or parenterally administered to an adult patient in a single dose of 0.001 to 500 mg once or in several divided times a day. Additionally, the dose can suitably be increased or reduced depending on the disease type to be treated, patient's age, body weight, symptoms, and the like.

Typical production methods of the compound (I) of the present invention are shown below in Schemes A and B.

The following methods are examples of the production method of the compounds of the present invention, and the present invention is not limited thereto. Additionally, in the following examples of the production method, the compounds may form a salt unless the reactions are affected.

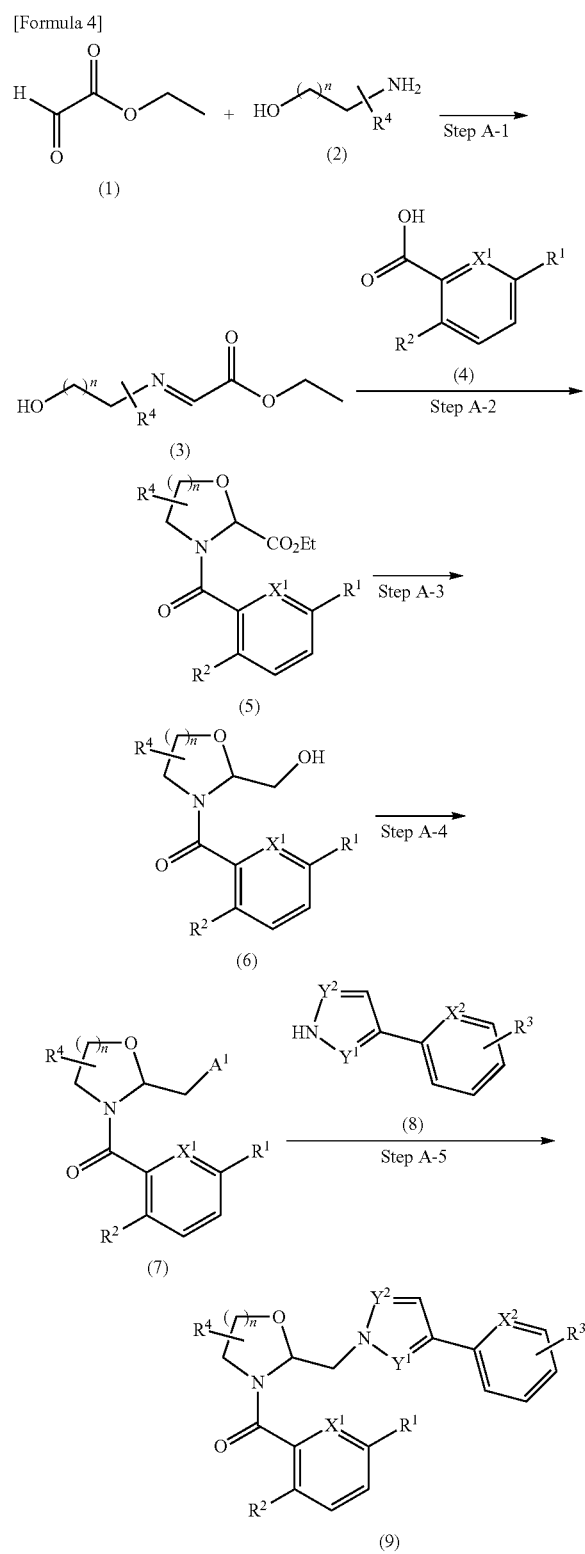

Scheme A

[Formula 4]

wherein $X^1$, $X^2$, $Y^1$, $Y^2$, $R^1$, $R^2$, $R^3$ and $R^4$ are as defined above. $A^1$ represents a halogen atom, a methanesulfonyloxy group, a p-toluenesulfonyloxy group or a trifluoromethanesulfonyloxy group. n is 1 or 2.

Step A-1: The compound (3) can be obtained by the condensation reaction of ethyl glyoxylate (1) and the amine compound (2). The reaction in Step A-1 can be carried out under the conditions in which a base is reacted with the amine compound or hydrochloride thereof in the presence or absence of a dehydrating agent such as molecular sieve or anhydrous copper sulfate in a solvent. Examples of the base to be used in the present reaction include organic amines such as pyridine, triethylamine and diisopropylethylamine, inorganic bases such as sodium hydroxide, potassium hydroxide and sodium hydrogen carbonate, and acetate such as sodium acetate and potassium acetate. Examples of the solvent to be used in the present reaction include ether solvents such as tetrahydrofuran and 1,4-dioxane, aprotic polar solvents such as N,N-dimethylformamide and acetonitrile, halogen solvents such as dichloromethane and chloroform, aromatic hydrocarbon solvents such as toluene, ethyl acetate, and mixed solvents thereof. The present reaction can be carried out at 0° C. to 100° C.

Step A-2: The compound (5) can be obtained by the condensation reaction of the compound (3) and the carboxylic acid (4). The reaction in Step A-2 can be carried out by a general amidation method of carboxylic acid. Examples include a method wherein carboxylic acid is converted to a carboxylic acid halide such as carboxylic acid chloride or carboxylic acid bromide and subsequently reacted with (3), and a method wherein carboxylic acid is reacted with (3) in the presence of a dehydration condensation agent. These reactions can all be carried out in the presence or absence of a base in a solvent. Examples of the halogenating agent to be used in the present reaction can include thionyl chloride, oxalyl chloride, phosphorus oxychloride or phosphorus oxybromide. Also, examples of the dehydration condensation agent to be used in the present reaction include 1-ethyl-3-(3-dimethylaminopropyl)carbodiimide-hydrochloride (EDC-HCl), [O-(7-azabenzotriazol-1-yl)-N,N,N',N'-tetramethyluronium hexafluorophosphate] (HATU), propane phosphonic acid anhydride, dicyclohexyl carbodiimide (DDC), diphenylphosphoryl azide (DPPA) and carbonyldiimidazole (CDI), and an activator such as 1-hydroxybenzotriazole or hydroxysuccinimide may be used as necessary. Examples of the solvent to be used in the present reaction include ether solvents such as tetrahydrofuran and 1,4-dioxane, aprotic polar solvents such as N,N-dimethylformamide and acetonitrile, halogen solvents such as dichloromethane and chloroform, aromatic hydrocarbon solvents such as toluene, ethyl acetate or mixed solvents thereof. Examples of the base to be used in the present reaction include organic amines such as pyridine, triethylamine and diisopropylethylamine and inorganic bases such as potassium carbonate, sodium carbonate and sodium hydrogen carbonate. The present reaction can be carried out usually at 0° C. to 150° C., preferably 0° C. to 80° C.

Step A-3: The compound (6) can be obtained by the reduction reaction of the ester of the compound (5). The reaction in Step A-3 can be carried out under the conditions in which the compound (5) is reacted with a reducing agent such as lithium aluminium hydride, diisobutyl aluminium hydride, sodium borohydride or lithium borohydride in an alcohol solvent such as methanol or ethanol, an ether solvent such as tetrahydrofuran or 1,4-dioxane, an aromatic hydrocarbon solvent such as toluene or a mixed solvent thereof. The present reaction can be carried out at −80° C. to 150° C., preferably 0° C. to 25° C.

Step A-4: The compound (7) can be obtained by converting the hydroxy group of the compound (6) to a general leaving group. Examples of the reaction in Step A-4 include chlorination, bromination, iodization, methanesulfonyloxylation and p-toluenesulfonyloxylation. An example of the chlorination reaction includes a method wherein a leaving group is obtained using, for example, methanesulfonyl chloride, or the like, followed by substitution with a chlorine atom. A method which uses carbon tetrachloride and triphenyl phosphine and a method which uses thionyl chloride or phosphorus oxychloride are further included. During these procedures, a chloride such as sodium chloride or potassium chloride may be added. An example of the bromination reaction includes a method wherein, for example, carbon tetrabromide and triphenyl phosphine are used. An example of the iodization reaction includes a method wherein, for example, iodine, triphenyl phosphine and imidazole are used. The methanesulfonyloxylation and p-toluenesulfonyloxylation can be achieved using, for example, methanesulfonyl chloride, p-toluenesulfonyl chloride, or the like, respectively. During these reactions, a suitable base may be added. Examples of the base to be added include organic bases such as triethylamine and diisopropylethylamine or inorganic bases such as potassium carbonate. Examples of the reaction solvent include ether solvents such as tetrahydrofuran and 1,4-dioxane, aprotic polar solvents such as N,N-dimethylformamide and acetonitrile, halogen solvents such as dichloromethane and chloroform, acetonitrile or mixed solvents thereof, and therein the reactions can be carried out under the temperature condition of about −80° C. to about the boiling point of such a solvent.

Step A-5: The compound (9) can be obtained by the reaction of the compound (7) and the compound (8). The reaction in Step A-5 proceeds in an alcohol solvent such as methanol and ethanol, an ether solvent such as tetrahydrofuran and 1,4-dioxane, an aprotic polar solvent such as N,N-dimethylformamide and acetonitrile, a halogen solvent such as dichloromethane and chloroform, dimethyl sulfoxide, acetonitrile, water or a mixed solvent thereof, in the presence of an inorganic base such as sodium hydride, sodium hydroxide, sodium carbonate, potassium carbonate or cesium carbonate, an alkali metal such as sodium ethoxide or potassium tert-butoxide, or an organic base such as a lower alkoxide of the alkaline earth metal, under the temperature condition of about −80° C. to about the boiling point of such a solvent.

Scheme B

[Formula 5]

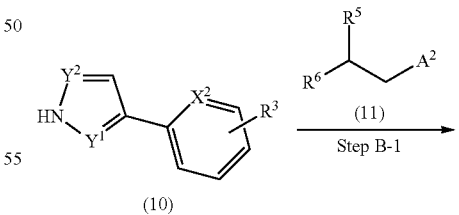

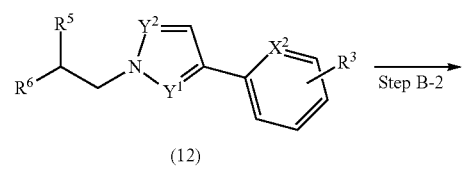

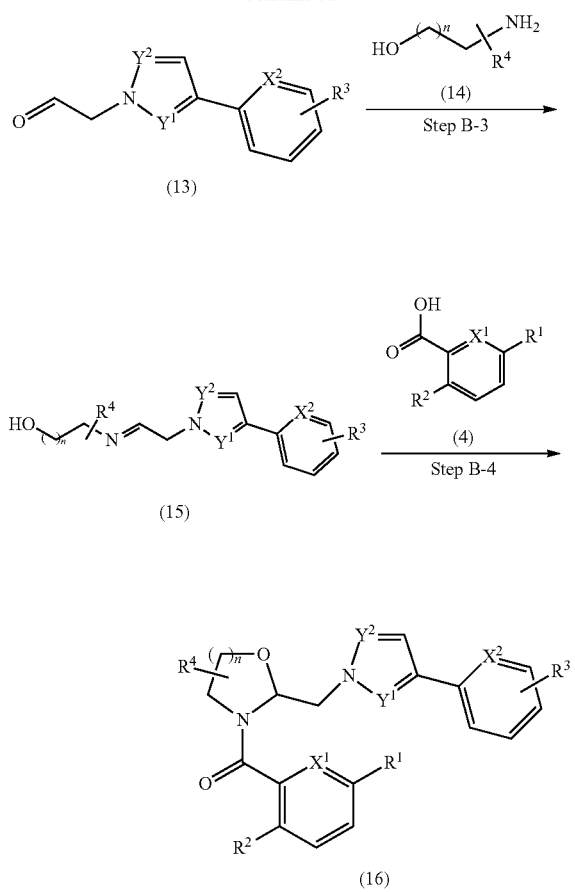

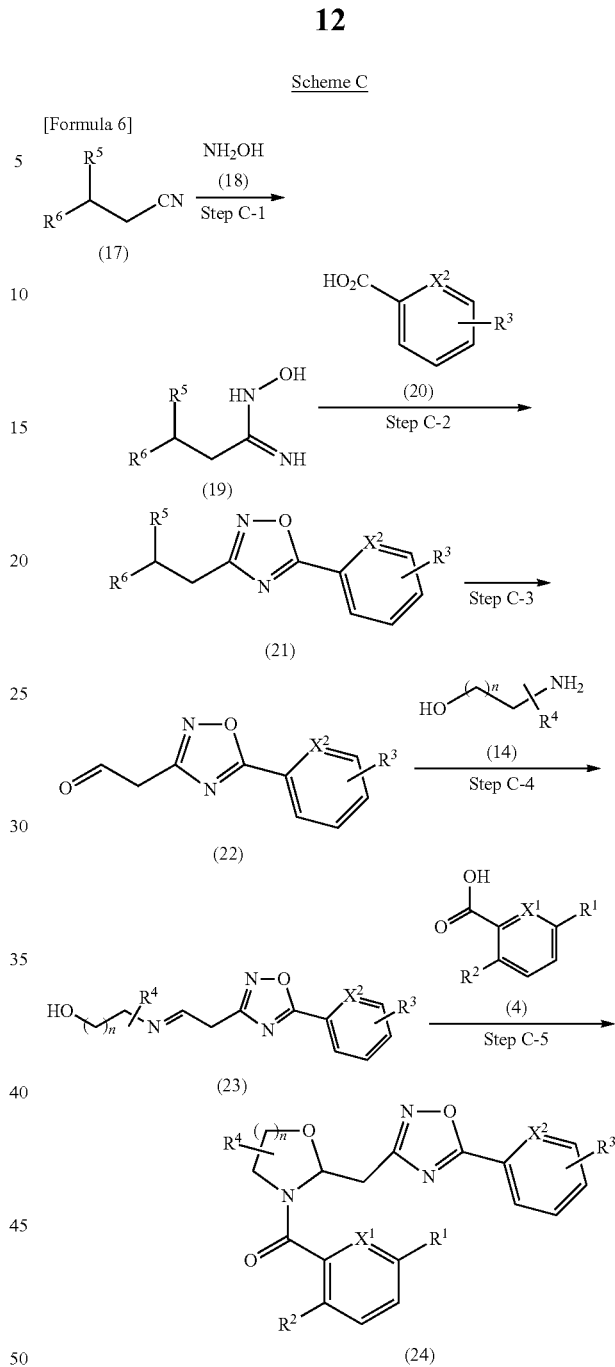

wherein $X^1$, $X^2$, $Y^1$, $Y^2$, $R^1$, $R^2$, $R^3$ and $R^4$ are as defined above. $R^5$ and $R^6$ represent an alkoxy group, and $A^2$ represents a halogen atom, a methanesulfonyloxy group, a p-toluenesulfonyloxy group or a trifluoromethanesulfonyloxy group.

Step B-1: The compound (12) can be obtained by the reaction of the compound (10) and the compound (11). The reaction in Step B-1 can be carried out in accordance with the same reaction conditions as in Step A-5.

Step B-2: The compound (13) can be obtained from the compound (12). The reaction in Step B-2 can be carried out under the conditions in which the compound (12) is reacted with an acid such as hydrochloric acid, trifluoroacetic acid or p-toluenesulfonic acid in a water containing alcohol solvent such as water containing methanol or water containing ethanol, an ether solvent such as tetrahydrofuran or 1,4-dioxane, a halogen solvent such as dichloromethane or chloroform, a ketone solvent such as acetone, water or a mixed solvent thereof. The present reaction can be carried out at 0° C. to 80° C.

Step B-3: The compound (15) can be obtained by the condensation reaction of the compound (13) and the compound (14). The reaction in Step B-3 can be carried out in accordance with the same reaction conditions as in Step A-1.

Step B-4: The compound (16) can be obtained by the condensation reaction of the compound (4) and the compound (15). The reaction in Step B-4 can be carried out in accordance with the same reaction conditions as in Step A-2.

wherein $X^1$, $X^2$, $R^1$, $R^2$, $R^3$ and $R^4$ are as defined above. $R^5$ and $R^6$ represent an alkoxy group.

Step C-1: The compound (19) can be obtained by the amidoximation reaction of the compound (17). The reaction in Step C-1 can be carried out under the conditions in which the nitrile compound (17) is reacted with the hydroxylamine (18) or hydrochloride thereof in an alcohol solvent such as methanol or ethanol. The present reaction can be carried out at 0° C. to 100° C.

Step C-2: The compound (21) can be obtained by the oxadiazole cyclization reaction of the compound (19) and the compound (20). The reaction in Step C-2 can be carried out under the conditions in which the compound (19) is reacted with the carboxylic acid (20) and a dehydration condensation agent such as 1-ethyl-3-(3-dimethylaminopropyl)carbodiimide-hydrochloride (EDC-HCl), dicyclohexylcarbodiimide (DDC), carbonyldiimidazole (CDI) in an ether solvent such as tetrahydrofuran or 1,4-dioxane, an aprotic polar solvent such as N,N-dimethylformamide, a halogen solvent such as dichloromethane or chloroform, an aromatic hydrocarbon solvent such as toluene, ethyl acetate, acetonitrile or a mixed solvent thereof. The present reaction is carried out usually at 0° C. to 150° C., preferably 0° C. to 90° C.

Step C-3: The compound (22) can be obtained by the acid hydrolysis of the compound (21).

The reaction in Step C-3 can be carried out in accordance with the same reaction conditions as in Step B-2.

Step C-4: The compound (23) can be obtained by the condensation reaction of the compound (14) and the compound (22). The reaction in Step C-4 can be carried out in accordance with the same reaction conditions as in Step A-1.

Step C-5: The compound (24) can be obtained by the condensation reaction of the compound (4) and the compound (23). The reaction in Step C-5 can be carried out in accordance with the same reaction conditions as in Step A-2.

Scheme D

[Formula 7]

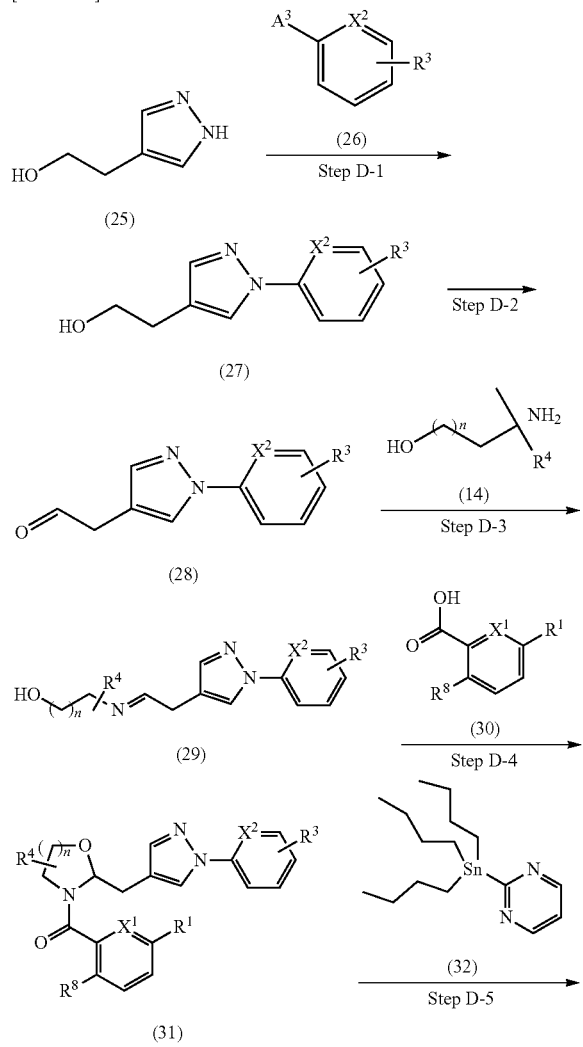

-continued

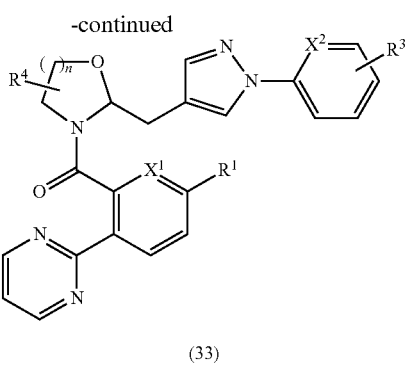

(33)

wherein $X^1$, $X^2$, $R^1$, $R^3$ and $R^4$ are as defined above. $R^8$ represents a triazolyl group, a pyridyl group or a halogen atom, and $A^3$ represents a halogen atom.

Step D-1: The compound (27) can be obtained by the nucleophilic reaction or coupling reaction of the compound (25) and the compound (26). The reaction in Step D-1 can be carried out in accordance with the same nucleophilic reaction conditions as in Step A-5. The coupling reaction can be carried out by a general method in which the nitrogen atom of the azole compound is substituted with an aromatic ring using a catalyst and a ligand in the presence of a base. Examples include the method described in Synlett, 2003, 15, 2428-2439 or a method in accordance therewith. Examples of the catalyst to be used in the present reaction include copper catalyst such as copper (O), copper (I) iodine, copper (I) chloride and copper (I) oxide. Examples of the ligand to be used in the present reaction include N,N'-dimethylethylenediamine, N,N'-dimethylcyclohexane-1,2-diamine, 2-aminopyridine, 1,10-phenanthroline and 2-hydroxybenzaldehyde oxime. Examples of the base to be used in the present reaction include potassium carbonate, potassium phosphate, potassium hydroxide, potassium tert-butoxide, cesium carbonate, sodium carbonate, sodium bicarbonate, sodium acetate, sodium methoxide and tetrabutyl ammonium hydroxide. Examples of the solvent to be used in the present reaction include alcohol solvents such as methanol and ethanol, ether solvents such as tetrahydrofuran and 1,4-dioxane, aprotic polar solvents such as N,N-dimethylformamide, dimethyl sulfoxide and acetonitrile, halogen solvents such as dichloromethane and chloroform, aromatic hydrocarbon solvents such as toluene, water or mixed solvents thereof. The present reaction can be carried out usually at 0° C. to 150° C., preferably 25° C. to 100° C.

Step D-2: The compound (28) can be obtained by the oxidation reaction of the hydroxyl group of the compound (27). The reaction in Step D-2 can be carried out under the conditions in which the compound (27) is reacted with a hypervalent iodine compound such as Dess-Martin reagent or 2-iodoxybenzoic acid, chromate such as pyridinium chlorochromate or pyridinium dichromate, or an oxidizing agent such as tetrapropylammonium perruthenate or manganese dioxide in a halogen solvent such as dichloromethane or chloroform, or an aprotic polar solvent such as dimethyl sulfoxide or acetonitrile. The present reaction can be carried out at 0° C. to 150° C., preferably 25° C. to 80° C.

Step D-3: The compound (29) can be obtained by the condensation reaction of the compound (14) and the compound (28). The reaction in Step D-3 can be carried out in accordance with the same reaction conditions as in Step A-1.

Step D-4: The compound (31) can be obtained by the condensation reaction of the compound (29) and the compound (30). The reaction in Step D-4 can be carried out in accordance with the same reaction conditions as in Step A-2.

Step D-5: The compound (33) can be obtained by the coupling reaction of the compound (31) and the compound (32). The reaction in Step D-5 can be obtained under the conditions of Stille coupling reaction in which the reaction is carried out using an organic tin compound in an aprotic polar solvent such as N,N-dimethylformamide, an aromatic hydrocarbon solvent such as toluene or a mixed solvent thereof. The comprehensive overview of the Stille coupling reaction can be found, for example, in Angew. Chem. Int. Ed., 43, 4704, (2004).

Scheme E

[Formula 8]

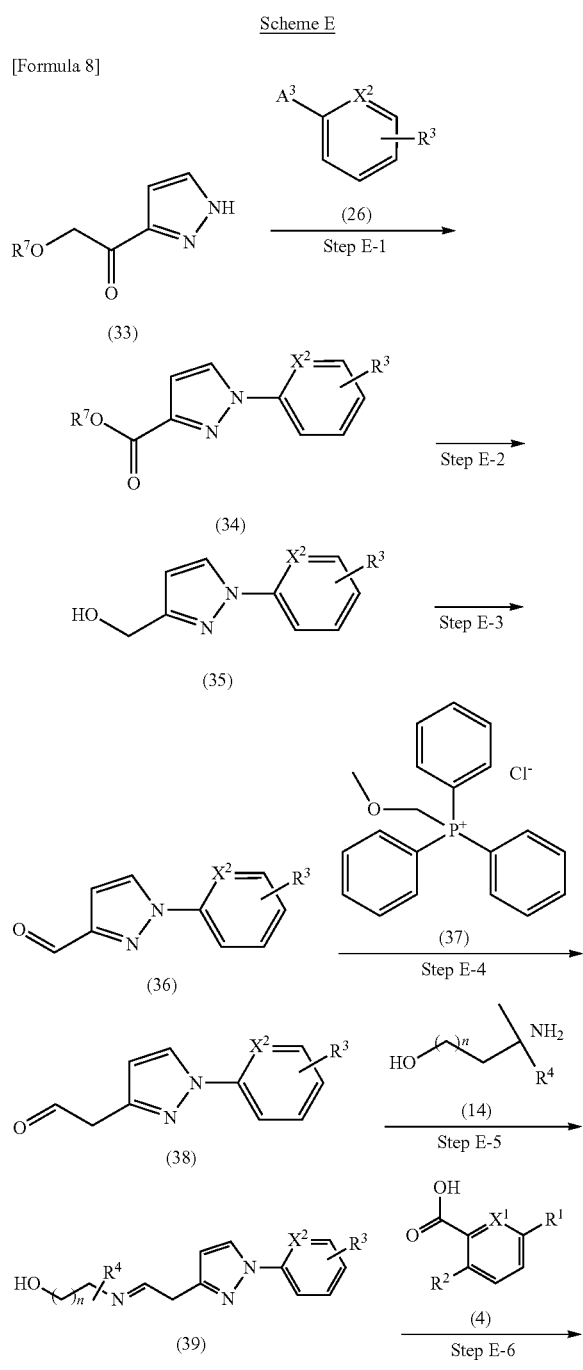

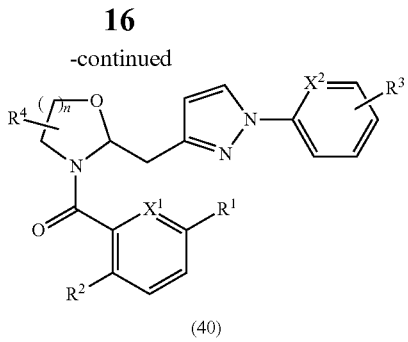

(40)

wherein $X^1$, $X^2$, $R^1$, $R^2$, $R^3$, $R^4$ and $A^3$ are as defined above. $R^7$ represents a common protective group of carboxylic acid, for example, the groups described in Protective Groups in Organic Chemistry, written by J. F. W. McOmie and Protective Groups in Organic Synthesis written by T. W. Greene and P. G. M. Wuts, and represents a $C_{1-6}$ alkyl group and a benzyl group, for example.

Step E-1: The compound (34) can be obtained by the nucleophilic reaction or coupling reaction of the compound (26) and the compound (33). The reaction in Step E-1 can be carried out in accordance with the same reaction conditions as in Step D-1.

Step E-2: The compound (35) can be obtained by the reduction reaction of the ester of the compound (34). The reaction in Step E-2 can be carried out under the conditions in which the compound (34) is reacted with a reducing agent such as lithium aluminium hydride, diisobutyl aluminium hydride, sodium borohydride or lithium borohydride in an alcohol solvent such as methanol or ethanol, an ether solvent such as tetrahydrofuran or 1,4-dioxane, an aromatic hydrocarbon solvent such as toluene or a mixed solvent thereof. The present reaction can be carried out at −80° C. to 150° C., preferably 0° C. to 25° C.

Step E-3: The compound (36) can be obtained by the oxidation reaction of the hydroxyl group of the compound (35). The reaction in Step E-3 can be carried out in accordance with the same reaction conditions as in Step D-2.

Step E-4: The compound (38) can be obtained by the Wittig reaction of the compound (36) and the compound (37). The reaction in Step E-4 can be carried out under the conditions in which methoxy methyl triphenyl phosphonium chloride is treated with a base such as sodium hydride, potassium hydride, tert-butoxypotassium, sodiumbis(trimethylsilyl)amide or lithiumbis(trimethylsilyl)amide in an ether solvent such as tetrahydrofuran or 1,4-dioxane, an aromatic hydrocarbon solvent such as toluene or a mixed solvent thereof, followed by being reacted with aldehyde. The present reactions can be carried out at 0° C. to 120° C. The reaction can be carried out under the conditions in which the produced enol ether is hydrolyzed using an inorganic acid such as hydrochloric acid, trifluoroacetic acid or p-toluenesulfonic acid, an organic acid or Lewis acid such as mercury acetate. The present reaction can be carried out at 0° C. to 80° C.

Step E-5: The compound (39) can be obtained by the condensation reaction of the compound (14) and the compound (38). The reaction in Step E-5 can be carried out in accordance with the same reaction conditions as in Step A-1.

Step E-6: The compound (40) can be obtained by the condensation reaction of the compound (4) and the compound (39). The reaction in Step E-6 can be carried out in accordance with the same reaction conditions as in Step A-2.

Scheme F

[Formula 9]

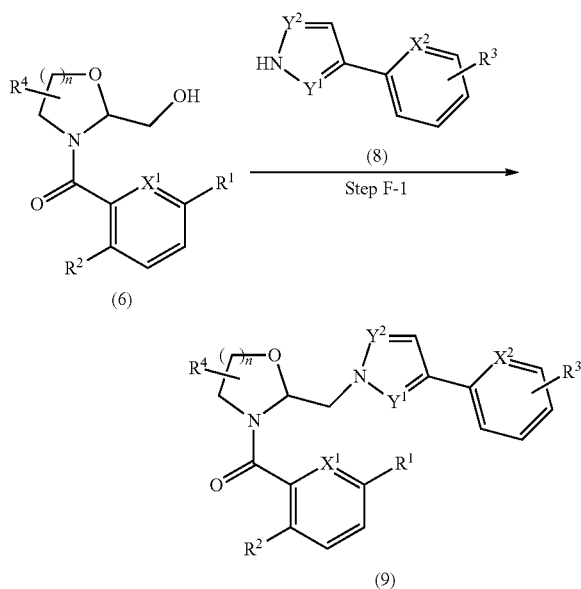

wherein $X^1$, $X^2$, $Y^1$, $Y^2$, $R^1$, $R^2$, $R^3$ and $R^4$ are as defined above.

Step F-1: The compound (9) can be obtained by the Mitsunobu reaction of the compound (6) and the compound (8). The reaction in Step F-1 can be carried out under the conditions in which the compounds (6) and (8) are reacted with triphenyl phosphine/diethyl azodicarboxylate (DEAD), cyanomethylene tributylphosphorane (CMBP) or the like in an ether solvent such as tetrahydrofuran or 1,4-dioxane, a halogen solvent such as dichloromethane or chloroform or a mixed solvent thereof. The present reaction can be carried out at 0° C. to 150° C., preferably 0° C. to 80° C.

Scheme G

[Formula 10]

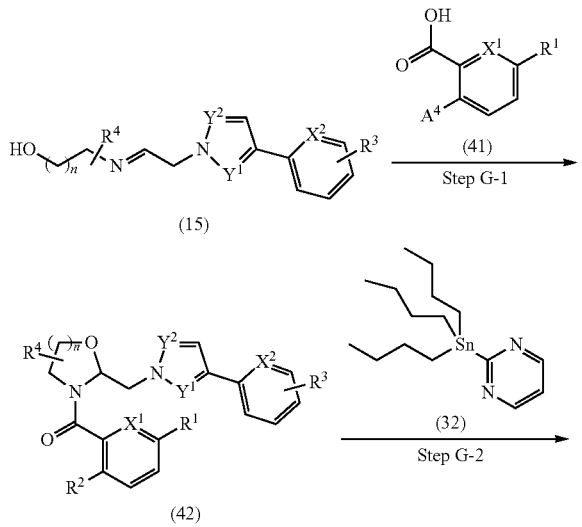

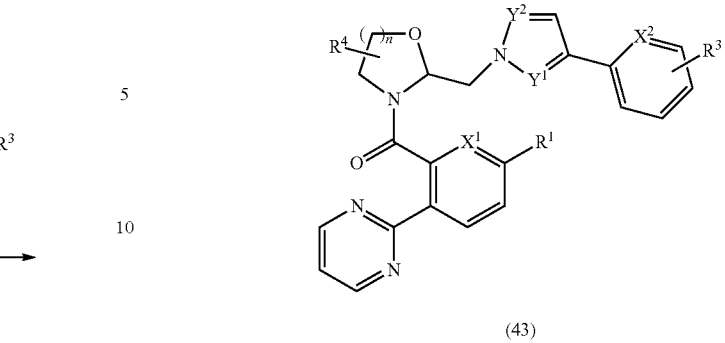

wherein $X^1$, $X^2$, $Y^1$, $Y^2$, $R^1$, $R^3$ and $R^4$ are as defined above. $A^4$ represents a halogen atom.

Step G-1: The compound (42) can be obtained by the condensation reaction of the compound (15) and the compound (41). The reaction in Step G-1 can be carried out in accordance with the same reaction conditions as in Step A-2.

Step G-2: The compound (43) can be obtained by the coupling reaction of the compound (32) and the compound (42). The reaction in Step G-2 can be carried out in accordance with the same reaction conditions as in Step D-5.

Scheme H

[Formula 11]

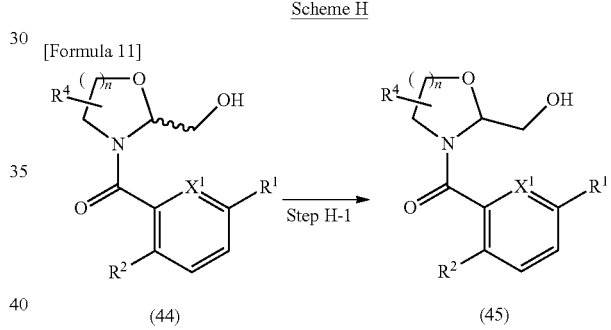

wherein $X^1$, $R^1$, $R^2$ and $R^4$ are as defined above.

Step H-1: The compound (45) can be obtained by separating an optical isomer of the compound (44). An optical isomer, in Step H-1, can directly be separated by HPLC equipped with a polysaccharide derivative chiral column, a protein based chiral column or the like. Further, examples include methods which use an enzyme method or a chemosynthesis method and a method in which an optical resolving agent is reacted to separate a diastereomer and converted to alcohol. With the method which uses an enzyme method, an optically active substance can be prepared by dissolving a compound in a solvent and acylating alcohol with the addition of lipase in the presence of acid alkenyl ester. The lipase to be used may be those derived from microorganisms or those derived from animals, and examples include pig pancreas lipases, and those derived from the genus *Candida*, the genus *Pseudomonas* and the genus *Aspergillus*. Examples of the acid alkenyl ester include vinyl acetate ester, vinyl propionate ester and vinyl hexanoate ester. Examples of the reaction solvent include ether solvents such as tetrahydrofuran and 1,4-dioxane, aprotic polar solvents such as acetonitrile, halogen solvents such as dichloromethane and chloroform, aromatic hydrocarbon solvents such as toluene, water and mixed solvents thereof. The present reaction can be carried out at 20° C. to 50° C., preferably 25° C. to 35° C.

With the synthesis method which uses a chemistry method, an optically active substance can be prepared by asymmetric esterification using an asymmetric catalyst and an esterifying agent. Examples of the asymmetric catalyst include optically active bisoxazoline-copper complexes. Examples of the optically active bisoxazoline catalyst include (R,R)-2,2'-isopropylidenebis(4-phenyl-2-oxazoline) and (S,S)-2,6-bis(4-isopropyl-2-oxazolin-2-yl)pyridine, and examples of the copper catalyst include copper halides such as trifluorocopper methanesulfonate(II), copper(II) chloride and copper(II) bromide. Examples of the esterifying agent include benzoyl chloride and acetyl chloride. Examples of the reaction solvent include alcohol solvents such as methanol and ethanol, ether solvents such as tetrahydrofuran and 1,4-dioxane, aprotic polar solvents such as acetonitrile, halogen solvents such as dichloromethane and chloroform, aromatic hydrocarbon solvents such as toluene and mixed solvents thereof. The present reaction can be carried out at −30° C. to 60° C., preferably −10° C. to 30° C.

With the diastereomer separation method, an optically active substance can be prepared by reacting an optical resolving agent containing a chiral carboxylic acid such as (S)-5-allyl-2-oxabicyclo[3.3.0]oct-8-ene or (−)-O-acetyl-D-mandelic acid to a compound, separating a diastereomer by fractional crystallization or column chromatography, followed by detachment of the optical resolving agent under the condition of an acid such as hydrochloric acid, trifluoroacetic acid or p-toluenesulfonic acid, or a base such as potassium carbonate, potassium phosphate or potassium hydroxide. The present reaction can be carried out at 0° C. to 80° C., preferably 0° C. to 30° C.

EXAMPLES

Hereinafter, the present invention is further described in details with reference to Reference Examples, Examples and Test Examples, but is not limited thereto, and changes may be made without departing from the scope of the present invention.

In Reference Examples and Examples below, the purification by column chromatography was performed using SNAP-Cartridge KP-Sil from Biotage for the "KP-Sil", SNAPCartridge HP-Sil from Biotage for the "HP-Sil", and SNAPCartridge KP-NH from Biotage for the "KP NH". For the aftertreatment operation in the following Reference Examples and Examples, ISOLUTE Phase Separator from Biotage was used for the "ISOLUTE Phase Separator".

In Reference Examples and Examples below, the purification by thin layer chromatography (PTLC) was performed using Silica gel 60F254 (Merck KGaA).

In Reference Examples and Examples below, the purification by preparative high performance liquid chromatography (HPLC) was carried out under the following conditions. However, for the case of a compound having a basic functional group and when trifluoroacetic acid is used in the present operation, a neutralization operation, or the like, may sometimes be carried out to obtain a free form.

Device: Trilution LC from Gilson
Column: SunFire prep C18 OBD 5.0 μm 30×50 mm from Waters, or YMC-Actus Triant 5.0 μm 50×30 mm from YMC
Solvent: Liquid A; 0.1% trifluoroacetic acid containing water, Liquid B; 0.1% trifluoroacetic acid containing acetonitrile
Gradient: 0 min. (Liquid A/Liquid B=90/10), 11 min. (Liquid A/Liquid B=20/80), 12 to 13.5 min. (Liquid A/Liquid B=5/95)
Flow rate: 40 mL/min.
Detection method: UV 254 nm In Reference Examples and Examples below, high performance liquid chromatography mass spectrum (HPLC) were measured by the following 2 conditions.

Condition 1
Measurement Instrument: Agilent 2900 and Agilent 6150 from Agilent
Column: Acquity CSH C18 1.7 μm 2.1×50 mm from Waters
Solvent: Liquid A; 0.1% formic acid containing water, Liquid B; 0.1% formic acid containing acetonitrile
Gradient: 0 min. (Liquid A/Liquid B=80/20), 1.2 to 1.4 min. (Liquid A/Liquid B=1/99).
Flow rate: 0.8 mL/min., Detection method: UV 254 nm
Ionization method: Electron impact ionization method (ESI: Electron Spray Ionization)

Condition 2
Measurement Instrument: LCMS-2010EV from SHIMADZU
Column: Shim-pack XR-ODS 2.2 μm 2.0 mmI.D.×30 mm from SHIMADZU
Solvent: Liquid A; 0.1% formic acid containing water, Liquid B; 0.1% formic acid containing acetonitrile
Gradient: 0 min. (Liquid A/Liquid B=90/10), 1 min. (Liquid A/Liquid B=60/40), 2 min.
(Liquid A/Liquid B=0/100), 2.5 min. (Liquid A/Liquid B=0/100)
Flow rate: 0.6 mL/min, Detection method: UV 254 nm
Ionization method: Electron impact ionization method (ESI: Electron Spray Ionization) and Atmospheric Pressure Chemical Ionization (APCI: Atmospheric Pressure Chemical Ionization)

In Reference Examples and Examples below, the mass spectrum (MS) was measured under the following conditions.
MS Measurement Instrument: LCMS-2010EV from SHIMADZU or Platform LC from micromass In Examples below, the analysis of racemic compounds was carried out by either one of the following 13 conditions.

Condition 1
Measurement Instrument: Agilent 1100 from Agilent
Column: CHIRALPAK AD-3 (Daicel Corporation, 4.6 mm*250 mm)
Flow rate: 1.0 mL/min
Mobile phase: Hexane/ethanol=30/70

Condition 2
Measurement Instrument: Waters 2695 and 2998 from Waters
Column: CHIRALPAK IB (Daicel Corporation, 4.6 mm*250 mm)
Flow rate: 1.0 mL/min
Mobile phase: Hexane/ethanol=90/10

Condition 3
Measurement Instrument: Waters 2695 and 2998 from Waters
Column: CHIRALPAK IB (Daicel Corporation, 4.6 mm*250 mm)
Flow rate: 1.0 mL/min
Mobile phase: Hexane/2-propanol=30/70

Condition 4
Measurement Instrument: Agilent 1100 from Agilent
Column: CHIRALPAK AD-3 (Daicel Corporation, 4.6 mm*150 mm)
Flow rate: 1.0 mL/min
Mobile phase: Hexane/ethanol=20/80

Condition 5
Measurement Instrument: Agilent 1100 from Agilent
Column: CHIRALPAK IB-3 (Daicel Corporation, 4.6 mm*150 mm)
Flow rate: 1.0 mL/min
Mobile phase: Hexane/ethanol=50/50
Condition 6
Measurement Instrument: Waters 996 and 2795 from Waters
Column: CHIRALPAK AD-3 (Daicel Corporation, 4.6 mm*150 mm)
Flow rate: 1.0 mL/min
Mobile phase: Hexane/2-propanol=0/100
Condition 7
Measurement Instrument: Agilent 1100 from Agilent
Column: CHIRALPAK IB-3 (Daicel Corporation, 4.6 mm*150 mm)
Flow rate: 1.0 mL/min
Mobile phase: Hexane/ethanol=70/30
Condition 8
Measurement Instrument: Waters 996 and 2795 from Waters
Column: CHIRALPAK IB-3 (Daicel Corporation, 4.6 mm*150 mm)
Flow rate: 1.0 mL/min
Mobile phase: Hexane/2-propanol=30/70
Condition 9
Measurement Instrument: Agilent 1100 from Agilent
Column: CHIRALPAK AD-3 (Daicel Corporation, 4.6 mm*150 mm)
Flow rate: 1.0 mL/min
Mobile phase: Hexane/ethanol=30/70
Condition 10
Measurement Instrument: Agilent 1100 from Agilent
Column: CHIRALPAK IB-3 (Daicel Corporation, 4.6 mm*150 mm)
Flow rate: 1.0 mL/min
Mobile phase: Hexane/ethanol=90/10
Condition 11
Measurement Instrument: Agilent 1100 from Agilent
Column: CHIRALPAK IB-3 (Daicel Corporation, 4.6 mm*150 mm)
Flow rate: 1.0 mL/min
Mobile phase: Hexane/ethanol=80/20
Condition 12
Measurement Instrument: Waters 996 and 2795 from Waters
Column: CHIRALPAK ID-3 (Daicel Corporation, 4.6 mm*150 mm)
Flow rate: 1.0 mL/min
Mobile phase: Hexane/2-propanol=50/50
Condition 13
Measurement Instrument: Waters 996 and 2795 from Waters
Column: CHIRALPAK IA-3 (Daicel Corporation, 4.6 mm*150 mm)
Flow rate: 1.0 mL/min
Mobile phase: Hexane/2-propanol=20/80
In Examples below, the optical rotation analysis was measured under the following conditions.
Measurement Instrument: JASCO P-2300 from JASCO
In Reference Examples and Examples below, Initiator (Biotage AB) was used as the microwaves synthesizer.

In Reference Examples and Examples below, the compounds were named in accordance with ACD/Name (ACD/Labs 12.01, Advanced Chemistry Development Inc.).

In Reference Examples and Examples, the following terms and reagents are shown as follows.

$Na_2SO_4$ (anhydrous sodium sulfate), $MgSO_4$ (anhydrous magnesium sulfate), $Cs_2CO_3$ (cesium carbonate), $NaHCO_3$ (sodium bicarbonate), TFA (trifluoroacetic acid), THF (tetrahydrofuran), DMF (N,N-dimethylformamide), NMP (N-methyl-2-pyrrolidone), EtOAc (ethyl acetate), $CHCl_3$ (chloroform), HATU [O-(7-azabenzotriazol-1-yl)-N,N,N',N'-tetramethyluronium hexafluorophosphate], DIPEA (N,N-diisopropylethylamine), TEA (triethylamine), MsCl (methanesulfonyl chloride), $NaBH_4$ (sodium borohydride), $LiBH_4$ (lithium borohydride).

Reference Example 1

(±)-Ethyl 3-[5-methyl-2-(2H-1,2,3-triazol-2-yl)benzoyl]-1,3-oxazolidine-2-carboxylate

[Formula 12]

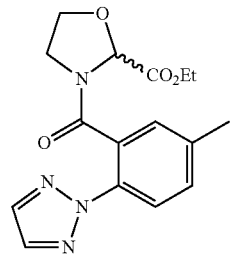

To a solution of ethyl glyoxylate (polymer type, a solution of 47% toluene) (13.4 mL, 63.5 mol) in $CHCl_3$ (260 mL), activated molecular sieve 4 A (200 g) and 2-aminoethanol (4.0 mL, 66.1 mmol) were added and the resulting mixture was stirred at room temperature for 24 hours. The molecular sieve 4 A was filtered off through Celite®, and then the solvent was distilled off under reduced pressure to obtain a pale yellow oil. To a solution of 5-methyl-2-(2H-1,2,3-triazol-2-yl)benzoic acid (2.7 g, 13.2 mmol) in $CHCl_3$ (130 mL), thionyl chloride (1.4 mL, 19.8 mmol) was added dropwise and stirred at 75° C. for 5 hours. The reaction mixture was allowed to cool to room temperature, and then the solvent and excess thionyl chloride were distilled off under reduced pressure. To a solution of the obtained residue in $CHCl_3$ (100 mL), a solution of TEA (3.7 mL, 26.4 mmol) and the pale yellow oil obtained in the above reaction in $CHCl_3$ (30 mL) was added under cooling with ice water, and the resulting mixture was heated to room temperature and stirred for 3 hours. Water was added to the reaction mixture, followed by extraction with $CHCl_3$. The organic layer was washed with a saturated aqueous solution of sodium chloride, dried over $Na_2SO_4$, then the drying agent was filtered off, and then the solvent was distilled off under reduced pressure. The obtained residue was purified by column chromatography (HP-Sil 150 g, hexane/EtOAc=88/12 to 0/100) to obtain the title compound (3.6 g) (pale yellow oil).

MS (ESI/APCI Dual pos.) m/z: 331 [M+H]$^+$

Reference Example 2

(±)-[2-(Hydroxymethyl)-1,3-oxazolidin-3-yl][5-methyl-2-(2H-1,2,3-triazol-2-yl)phenyl]methanone

[Formula 13]

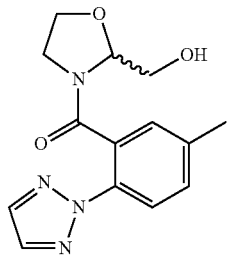

To a solution of (±)-ethyl 3-[5-methyl-2-(2H-1,2,3-triazol-2-yl)benzoyl]-1,3-oxazolidine-2-carboxylate obtained in Reference Example 1 (4.0 g, 12.1 mmol) in MeOH (60 mL), NaBH$_4$ (4.6 g, 121 mmol) was added gradually under cooling with ice water and stirred for 1 hour. The resulting mixture was heated to room temperature and stirred for 1 hour. The solvent was distilled off under reduced pressure, a saturated aqueous solution of ammonium chloride was added to the reaction mixture, which was extracted with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 100 g, hexane/EtOAc=88/12 to 0/100) to obtain the title compound (3.6 g) (colorless oil).

MS (ESI/APCI Dual pos.) m/z: 289 [M+H]$^+$

Reference Example 3

(±)-Ethyl 3-[5-methyl-2-(2H-1,2,3-triazol-2-yl)benzoyl]-1,3-oxazinane-2-carboxylate

[Formula 14]

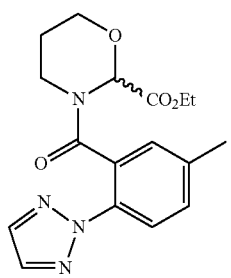

By using ethyl glyoxylate (polymer type, a solution of 47% toluene) (4.3 mL, 20.4 mol), 3-aminopropan-1-ol (1.6 mL, 20.4 mmol) and 5-methyl-2-(2H-1,2,3-triazol-2-yl)benzoic acid (1.0 g, 4.9 mmol), the same procedure as in Reference Example 1 was carried out to obtain the title compound (1.3 g) (colorless solid).

MS (ESI pos.) m/z: 367 [M+Na]$^+$

Reference Example 4

(±)-[2-(Hydroxymethyl)-1,3-oxazinan-3-yl][5-methyl-2-(2H-1,2,3-triazol-2-yl)phenyl]methanone

[Formula 15]

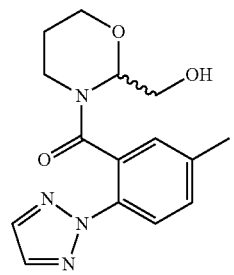

To a solution of (±)-ethyl 3-[5-methyl-2-(2H-1,2,3-triazol-2-yl)benzoyl]-1,3-oxazinane-2-carboxylate obtained in Reference Example 3 (0.50 g, 1.5 mmol) in THF (5 mL), a solution of LiBH$_4$ in THF (0.97 mL, 2.9 mmol) was added and stirred for 2 hours at room temperature. Water was added to the reaction mixture, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 25 g, hexane/EtOAc=88/12 to 0/100) to obtain the title compound (0.34 g) (colorless oil).

MS (ESI pos.) m/z: 303 [M+H]$^+$

Reference Example 5

Ethyl(2RS,5S)-5-methyl-3-[5-methyl-2-(2H-1,2,3-triazol-2-yl)benzoyl]-1,3-oxazolidine-2-carboxylate

[Formula 16]

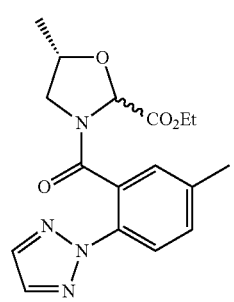

By using ethyl glyoxylate (polymer type, a solution of 47% toluene) (0.5 mL, 2.4 mmol), (2S)-1-aminopropan-2-ol (0.18 mL, 2.4 mmol) and 5-methyl-2-(2H-1,2,3-triazol-2-yl)benzoic acid (0.20 g, 0.98 mmol), the same procedure as in Reference Example 1 was carried out to obtain the title compound (0.11 g) (colorless oil).

MS (ESI/APCI Dual pos.) m/z: 345 [M+H]$^+$

Reference Example 6

Ethyl (2RS,5R)-5-methyl-3-[5-methyl-2-(2H-1,2,3-triazol-2-yl)benzoyl]-1,3-oxazolidine-2-carboxylate

[Formula 17]

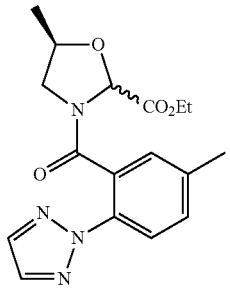

By using ethyl glyoxylate (polymer type, a solution of 47% toluene) (0.50 mL, 2.4 mmol), (2R)-1-aminopropan-2-ol (0.18 mL, 2.4 mmol) and 5-methyl-2-(2H-1,2,3-triazol-2-yl)benzoic acid (0.20 g, 0.98 mmol), the same procedure as in Reference Example 1 was carried out to obtain the title compound (0.14 g) (colorless oil).

MS (ESI/APCI Dual pos.) m/z: 345 [M+H]$^+$

Reference Example 7

[(2S,4R)-2-(hydroxymethyl)-4-methyl-1,3-oxazolidin-3-yl][5-methyl-2-(2H-1,2,3-triazol-2-yl)phenyl]methanone

[Formula 18]

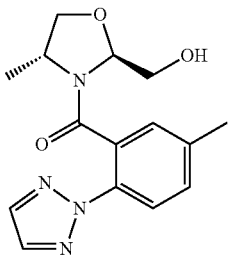

By using ethyl glyoxylate (polymer type, a solution of 47% toluene) (2.0 mL, 9.5 mmol), (2R)-2-aminopropan-1-ol (0.73 mL, 9.5 mmol) and 5-methyl-2-(2H-1,2,3-triazol-2-yl)benzoic acid (1.0 g, 4.9 mmol), the same procedure as in Reference Example 1 was carried out to obtain a diastereomer mixture of ethyl (2RS,4R)-4-methyl-3-[5-methyl-2-(2H-1,2,3-triazol-2-yl)benzoyl]-1,3-oxazolidine-2-carboxylate. The obtained diastereomer mixture was purified by thin layer chromatography (1 mm, hexane/EtOAc=66/34) to obtain ethyl (2S,4R)-4-methyl-3-[5-methyl-2-(2H-1,2,3-triazol-2-yl)benzoyl]-1,3-oxazolidine-2-carboxylate (colorless oil). By using the obtained colorless oil as the raw material, the same procedure as in Reference Example 4 was carried out to obtain the title compound (0.041 g) (colorless oil).

MS (ESI pos.) m/z: 303 [M+H]$^+$

Reference Example 8

[(2S,4S)-2-(Hydroxymethyl)-4-methyl-1,3-oxazolidin-3-yl][5-methyl-2-(2H-1,2,3-triazol-2-yl)phenyl]methanone

[Formula 19]

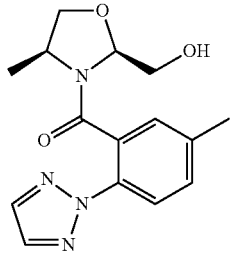

By using ethyl glyoxylate (polymer type, a solution of 47% toluene) (2.0 mL, 9.5 mmol), (2S)-2-aminopropan-1-ol (0.73 mL, 9.5 mmol) and 5-methyl-2-(2H-1,2,3-triazol-2-yl)benzoic acid (1.0 g, 4.9 mmol), the same procedure as in Reference Example 1 was carried out to obtain a diastereomer mixture of ethyl (2RS,4S)-4-methyl-3-[5-methyl-2-(2H-1,2,3-triazol-2-yl)benzoyl]-1,3-oxazolidine-2-carboxylate. The obtained diastereomer mixture was purified by thin layer chromatography (1 mm, hexane/EtOAc=66/34) to obtain ethyl (2S,4S)-4-methyl-3-[5-methyl-2-(2H-1,2,3-triazol-2-yl)benzoyl]-1,3-oxazolidine-2-carboxylate (colorless oil). By using the obtained colorless oil as the raw material, the same procedure as in Reference Example 4 was carried out to obtain the title compound (0.19 g) (colorless solid).

MS (ESI pos.) m/z: 303 [M+H]$^+$

Reference Example 9

5-Fluoro-2-[1-(tetrahydro-2H-pyran-2-yl)-1H-pyrazol-5-yl]pyridine

[Formula 20]

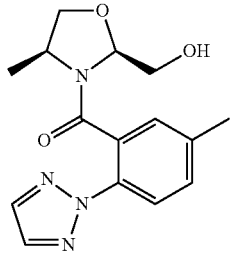

To a mixed solution of 1-(tetrahydro-2H-pyran-2-yl)-5-(4,4,5,5-tetramethyl-1,3,2-dioxaborolan-2-yl)-1H-pyrazole (100.5 g, 0.36 mol), 2-bromo-5-fluoropyridine (56.5 g, 0.33 mol), and Pd(PPh$_3$)$_4$ (38.0 g, 32.6 mmol) in ethanol (300 mL) and toluene (300 mL), a 2M aqueous solution of Na$_2$CO$_3$ (0.49 L, 0.99 mol) was added, and the resulting mixture was heated to reflux for 2 hours. The reaction mixture was allowed to cool to room temperature, then water and EtOAc were added thereto, and the resulting mixture was stirred at room temperature for 30 minutes, followed by extraction with EtOAc. The organic layer was washed with a saturated aqueous solution of sodium chloride, dried over MgSO$_4$, then the drying agent was filtered off, then NH silica gel (400 g) was added thereto, and the resulting mixture was stirred for 15 hours. The mixture was filtered through acid silica gel (eluted with n-hexane:AcOEt=1:1→AcOEt) and the solvent was distilled off under reduced pressure to obtain the title compound (100 g) (pale yellow oil).

MS (ESI pos.) m/z: 248 [M+H]+

Reference Example 10

5-Fluoro-2-(1H-pyrazol-3-yl)pyridine

[Formula 21]

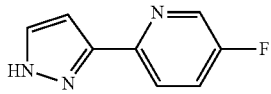

To a solution of 5-fluoro-2-[1-(tetrahydro-2H-pyran-2-yl)-1H-pyrazol-5-yl]pyridine obtained in Reference Example 9 (81.2 g, 0.33 mol) in methanol (250 mL), a 4M solution of HCl-EtOAc (0.25 L, 0.96 mol) was added, and the resulting mixture was stirred at room temperature for 16 hours. The solvent was distilled off under reduced pressure, then EtOAc (500 mL) was added to the residue, and the resulting mixture was heated to reflux for 1 hour. The reaction mixture was allowed to cool to room temperature, then ice-cooled, and then the precipitate was filtered out and dried to obtain a hydrochloride (colorless solid) of the title compound. Water (700 mL) and EtOAc (350 mL) were added to the obtained hydrochloride, and the resulting mixture was stirred for 30 minutes and then separated. The obtained organic layer was extracted with 1.2M hydrochloric acid (100 mL) three times. The aqueous layers were combined and the pH was adjusted to 12 with an 8M aqueous solution of NaOH, and then the organic layer was extracted with $CHCl_3$. The extracted organic layer was passed through an ISOLUTE Phase Separator, and the solvent was distilled off under reduced pressure. Diisopropyl ether (300 mL) was added to the obtained residue, and the resulting mixture was heated to reflux for 2 hours. The reaction mixture was allowed to cool at room temperature, then ice-cooled, and then the precipitate was filtered out and dried to obtain the title compound (44.9 g) (pale pink solid).

MS (ESI pos.) m/z: 164 [M+H]+

Reference Example 11

5-Fluoro-2-(1H-pyrazol-4-yl)pyridine

[Formula 22]

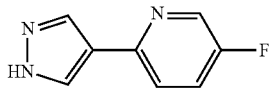

To a solution of tert-butyl 4-(4,4,5,5-tetramethyl-1,3,2-dioxaborolan-2-yl)-1H-pyrazole-1-carboxylate (15.4 g, 52.5 mmol) and 2-bromo-5-fluoropyridine (8.4 g, 47.7 mmol) in 1,4-dioxane (100 mL), $Pd(PPh_3)_4$ (5.5 g, 4.77 mmol) and a 2M aqueous solution of $Na_2CO_3$ (71.6 mL, 0.14 mol) were added, then the resulting mixture was stirred at 100° C. for 3 hours and then at room temperature for 72 hours. Water was added to the reaction mixture, followed by extraction with EtOAc. The organic layer was washed with a saturated aqueous solution of sodium chloride, dried over $MgSO_4$, then the drying agent was filtered off, and then the solvent was distilled off under reduced pressure. A small amount of EtOAc was added to the obtained residue and the resulting mixture was filtered out and dried to obtain the title compound (4.9 g) (colorless solid).

MS (ESI pos.) m/z: 164 [M+H]+

Reference Example 12

2-[1-(2,2-Diethoxyethyl)-1H-pyrazol-3-yl]-5-fluoropyridine

[Formula 23]

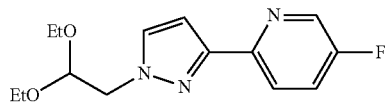

To a solution of 5-fluoro-2-(1H-pyrazol-3-yl)pyridine obtained in Reference Example 10 (11.7 g, 58.6 mmol) in DMF (195 mL), $Cs_2CO_3$ (57.3 g, 0.18 mol) and 2-bromo-1,1-diethoxyethane (11.5 mL, 76.2 mmol) were stirred for 18 hours at 80° C. The reaction mixture was allowed to cool to room temperature, then water was added thereto, followed by extraction with EtOAc. The organic layer was washed with a saturated aqueous solution of sodium chloride, dried over $MgSO_4$, then the drying agent was filtered off, and then the solvent was distilled off under reduced pressure. The obtained residue was purified by column chromatography (HP-Sil 50 g, hexane/EtOAc=88/12 to 35/65) to obtain the title compound (8.2 g) (colorless oil).

MS (ESI pos.) m/z: 280 [M+H]$^+$

Reference Examples 13 to 15 were obtained by the same procedure as in Reference Example 12. The structural formula, the names, and MS data of the obtained compounds are shown in Table 1.

TABLE 1

| Reference Example No. | Structural formula | Compound name | MS (ESI pos.) m/z |
|---|---|---|---|
| Reference Example 13 | | 2-[1-(2,2-diethoxyethyl)-1H-pyrazol-4-yl]-5-fluoropyridine | 280 (M + H)$^+$ |

| Reference Example No. | Structural formula | Compound name | MS (ESI pos.) m/z |
|---|---|---|---|
| Reference Example 14 | 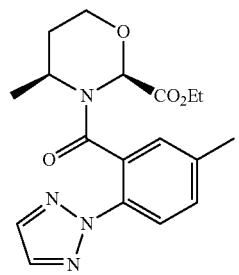 | 1-(2,2-diethoxyethyl)-3-(4-fluorophenyl)-1H-pyrazole | 205 (M + H)+ |
| Reference Example 15 | 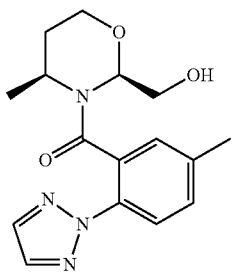 | 1-(2,2-diethoxyethyl)-4-(4-fluorophenyl)-1H-pyrazole | 205 (M + H)+ |

Reference Example 16

Ethyl (2S,4S)-4-methyl-3-[5-methyl-2-(2H-1,2,3-triazol-2-yl)benzoyl]-1,3-oxazinane-2-carboxylate

[Formula 24]

To a solution of (3R)-3-aminobutanoic acid (1.0 g, 9.7 mmol) in THF (10 mL), a solution of borane-THF in 0.9 mol/L (32.3 mL, 29.1 mmol) was added dropwise under cooling in an ice bath over a period of 1 hour, and the resulting mixture was stirred for 20 minutes at room temperature. The resulting mixture was heated to 80° C. and further stirred with heating for 6 hours. Methanol was added thereto under cooling in an ice bath, the reaction mixture was stirred for 30 minutes and then concentrated under reduced pressure. By using the obtained (3R)-3-aminobutan-1-ol, ethyl glyoxylate (polymer type, a solution of 47% toluene) (2.0 mL, 9.7 mmol) and 5-methyl-2-(2H-1,2,3-triazol-2-yl)benzoic acid (0.50 g, 2.5 mmol), the same procedure as in Reference Example 1 was carried out to obtain a diastereomer mixture (colorless oil). The obtained diastereomer mixture was purified by column chromatography (HP-Sil 10 g, hexane/EtOAc=90/10 to 0/100) to obtain the title compound (0.37 g), which was a low polar compound (colorless oil).

MS (ESI pos.) m/z: 359 [M+H]+

Reference Example 17

[(2S,4S)-2-(Hydroxymethyl)-4-methyl-1,3-oxazinan-3-yl][5-methyl-2-(2H-1,2,3-triazol-2-yl)phenyl]methanone

[Formula 25]

By using ethyl (2S,4S)-4-methyl-3-[5-methyl-2-(2H-1,2,3-triazol-2-yl)benzoyl]-1,3-oxazinane-2-carboxylate obtained in Reference Example 16 (0.37 g, 1.0 mmol), the same procedure as in Reference Example 2 was carried out to obtain the title compound (0.068 g) (colorless solid).

MS (ESI pos.) m/z: 317 [M+H]+

Reference Example 18

Ethyl(2RS,5RS)-5-methyl-3-[5-methyl-2-(2H-1,2,3-triazol-2-yl)benzoyl]-1,3-oxazinane-2-carboxylate

[Formula 26]

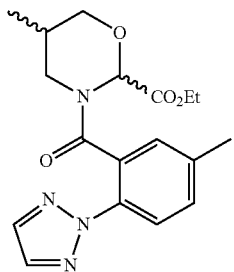

By using 3-amino-2-methylpropan-1-ol (0.10 g, 1.1 mmol), ethyl glyoxylate (polymer type, a solution of 47% toluene) (2.0 mL, 9.7 mmol) and 5-methyl-2-(2H-1,2,3-triazol-2-yl)benzoic acid (0.5 g, 2.5 mmol), the same procedure as in Reference Example 1 was carried out to obtain the title compound (0.13 g) (colorless oil).

MS (ESI pos.) m/z: 359 [M+H]$^+$

Reference Example 19

N-Hydroxy-3,3-dimethoxypropanimidamide

[Formula 27]

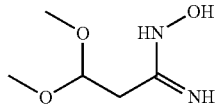

To a solution of hydroxylamine monohydrochloride (3.2 g, 45.6 mmol) in MeOH (70 mL), NaHCO$_3$ (3.8 g, 45.6 mmol) was added and stirred for 30 minutes at room temperature, and then a solution of 3,3-dimethoxypropanenitrile (5.0 g, 43.4 mmol) in MeOH (30 mL) was added dropwise thereto. The reaction mixture was stirred for 15 hours at 80° C. The mixture was allowed to cool to room temperature to filter off the salt produced, and the solvent was distilled off under reduced pressure. The obtained residue was purified by column chromatography (HP-Sil 100 g, CHCl$_3$/MeOH=99/1 to 90/10) to obtain the title compound (4.5 g) (pale yellow oil).

MS (ESI pos.) m/z: 171 [M+Na]$^+$

Reference Example 20

2-[3-(2,2-dimethoxyethyl)-1,2,4-oxadiazol-5-yl]-5-fluoropyridine

[Formula 28]

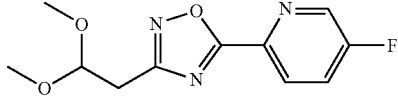

A solution of N-hydroxy-3,3-dimethoxypropanimidamide obtained in Reference Example 19 (1.0 g, 6.8 mmol) in DMF (3 mL) was added to a solution of 5-fluoropyridine-2-carboxylic acid (1.0 g, 7.1 mmol) and carbonyldiimidazole (1.3 g, 8.1 mmol) in DMF (4 mL), which was stirred for 1 hour at 40° C., and the mixture was stirred for 30 minutes. The reaction solution was heated to 90° C. and stirred for 15 hours. Water was added to the reaction mixture, followed by extraction with EtOAc. The organic layer was washed with water and a saturated aqueous solution of sodium chloride, dried over Na$_2$SO$_4$, then the drying agent was filtered off, and then the solvent was distilled off under reduced pressure. The obtained residue was purified by column chromatography (HP-Sil 25 g, hexane/EtOAc=75/25 to 0/100) to obtain the title compound (1.2 g) (colorless solid).

MS (ESI pos.) m/z: 254 [M+H]$^+$

Reference Example 21

3-(2,2-Dimethoxyethyl)-5-(4-fluorophenyl)-1,2,4-oxadiazole

[Formula 29]

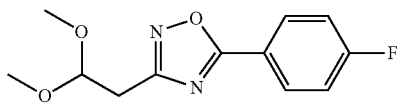

By using N-hydroxy-3,3-dimethoxypropanimidamide obtained in Reference Example 19 (1.0 g, 6.8 mmol) and 4-fluorobenzoic acid (0.99 g, 7.1 mmol) as the raw materials, the same procedure as in Reference Example 20 was carried out to obtain the title compound (1.4 g) (colorless oil).

MS (ESI pos.) m/z: 253 [M+H]$^+$

Reference Example 22

2-[1-(5-Fluoropyridin-2-yl)-1H-pyrazol-4-yl]ethanol

[Formula 30]

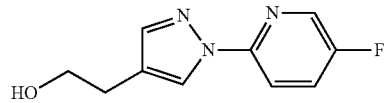

To a solution of 2-(1H-pyrazol-4-yl)ethanol (1.0 g, 8.9 mmol) and 2,5-difluoropyridine (0.89 mL, 9.8 mmol) in acetonitrile (45 mL), Cs$_2$CO$_3$ (9.7 g, 17.8 mmol) was added, and the resulting mixture was stirred for 3 hours at 80° C. The reaction mixture was allowed to cool, then water was added thereto, followed by extraction with EtOAc. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 25 g, hexane/EtOAc=90/10 to 30/70) to obtain the title compound (0.63 g) (colorless solid).

MS (ESI pos.) m/z: 208 [M+H]$^+$

Reference Example 23

(±)-(2-{[3-(4-Fluorophenyl)-1H-pyrazol-1-yl]methyl}-1,3-oxazinan-3-yl)(2-iodo-5-methylphenyl)methanone

[Formula 31]

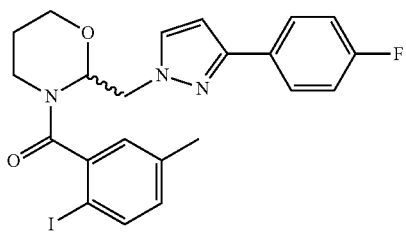

To a solution of 1-(2,2-diethoxyethyl)-3-(4-fluorophenyl)-1H-pyrazole obtained in Reference Example 14 (0.16 g, 0.57 mmol) in CHCl$_3$ (3 mL), TFA (0.42 mL, 5.7 mmol) was added, and the resulting mixture was stirred for 6 hours at 35° C. TFA (0.14 mL, 0.19 mmol) was further added thereto, and the mixture was stirred for 6 hours at 35° C. The reaction mixture was allowed to cool to room temperature, then an aqueous solution of NaHCO$_3$ was added to the reaction mixture, followed by extraction with CHCl$_3$. The organic layer was washed with a saturated aqueous solution of sodium chloride, dried over Na$_2$SO$_4$, then the drying agent was filtered off. The solvent was distilled off under reduced pressure to obtain a colorless oil. To a solution of the obtained colorless oil in CHCl$_3$ (3 mL), activated molecular sieve 4 A (0.60 g) and 3-aminopropan-1-ol (0.044 mL, 0.57 mmol) were added and the resulting mixture was stirred for 24 hours at room temperature. The molecular sieve 4 A was filtered off through Celite®, and then the solvent was distilled off under reduced pressure to obtain a pale yellow oil. To a solution of 2-iodo-5-methylbenzoylchloride (0.19 g, 0.69 mmol) in CHCl$_3$ (5 mL), a solution of TEA (0.20 mL, 1.4 mmol) and the pale yellow oil obtained in the above reaction in CHCl$_3$ (2 mL) was added under cooling with ice water, and the resulting mixture was heated to room temperature and stirred for 15 hours. Water was added to the reaction mixture, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 50 g, hexane/EtOAc=80/20 to 0/100) to obtain the title compound (0.19 g) (light yellow oil).

MS (ESI pos.) m/z: 506 [M+H]$^+$

Reference Example 24

(±)-(2-{[4-(4-Fluorophenyl)-1H-pyrazol-1-yl]methyl}-1,3-oxazinan-3-yl)(2-iodo-5-methylphenyl)methanone

[Formula 32]

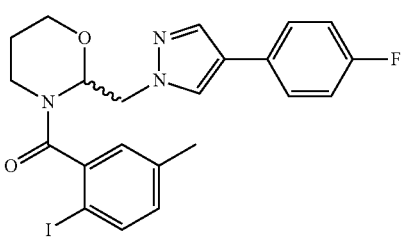

By using 1-(2,2-diethoxyethyl)-4-(4-fluorophenyl)-1H-pyrazole obtained in Reference Example 15 (1.0 g, 3.6 mmol) as the raw material, the same procedure as in Reference Example 23 was carried out to obtain the title compound (1.2 g) (colorless oil).

MS (ESI pos.) m/z: 506 [M+H]$^+$

Reference Example 25

(±)-(2-{[1-(5-Fluoropyridin-2-yl)-1H-pyrazol-4-yl]methyl}-1,3-oxazinan-3-yl)(2-iodo-5-methylphenyl)methanone

[Formula 33]

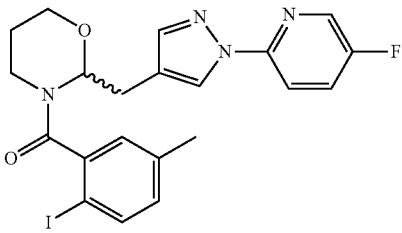

To a solution of 2-[1-(5-fluoropyridin-2-yl)-1H-pyrazol-4-yl]ethanol obtained in Reference Example 22 (0.21 g, 1.0 mmol) in dimethylsulfoxide (5 mL), 2-iodoxybenzoic acid (0.50 g, 1.1 mmol) was added, and the resulting mixture was stirred for 15 hours at room temperature. Water was added to the reaction mixture, followed by extraction with EtOAc. The organic layer was washed with water and a saturated aqueous solution of sodium chloride, dried over Na$_2$SO$_4$, then the drying agent was filtered off, and then the solvent was distilled off under reduced pressure to obtain a colorless oil. By using the obtained colorless oil as the raw material, the same procedure as in Reference Example 23 was carried out to obtain the title compound (0.16 g) (pale yellow oil).

MS (ESI pos.) m/z: 507 [M+H]$^+$

Reference Example 26

(±)-(5-Fluoro-2-iodophenyl)(2-{[1-(5-fluoropyridin-2-yl)-1H-pyrazol-4-yl]methyl}-1,3-oxazinan-3-yl)methanone

[Formula 34]

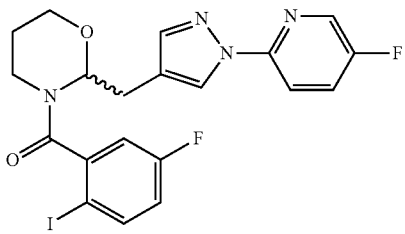

By using 2-[1-(5-fluoropyridin-2-yl)-1H-pyrazol-4-yl]ethanol obtained in Reference Example 22 (0.21 g, 1.0 mmol) and 5-fluoro-2-iodobenzoic acid (0.16 g, 0.60 mmol), the same procedure as in Reference Example 25 was carried out to obtain the title compound (0.15 g) (pale yellow oil).

MS (ESI pos.) m/z: 511 [M+H]+

Reference Example 27

Ethyl-1-(5-fluoropyridin-2-yl)-1H-pyrazol-3-carboxylate

[Formula 35]

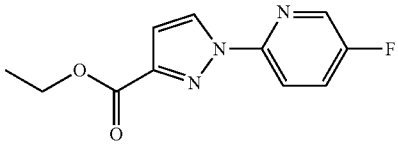

To a solution of ethyl-1H-pyrazole-3-carboxylate (25.0 g, 178.4 mmol) and 2-bromo-5-fluoropyridine (47.1 g, 267.6 mmol) in DMF (300 mL), copper(I) iodide (8.5 g, 44.6 mmol), rac-trans-N,N'-dimethylcyclohexane-1,2-diamine (28.1 mL, 178.4 mmol) and Cs2CO3 (116.2 g, 356.8 mmol) were added, and the resulting mixture was stirred for 7 hours at 90° C. The reaction mixture was allowed to cool to room temperature, then water and EtOAc were added thereto, followed by filtration through Celite®. The organic layer was taken out from the filtrate, washed with a saturated aqueous solution of sodium chloride, dried over Na2SO4, then the drying agent was filtered off, and then the solvent was distilled off under reduced pressure. The obtained residue was purified by column chromatography (HP-Sil 50 g, hexane/EtOAc=70/30 to 0/100). The obtained solid was stirred and washed in hexane/EtOAc=4/1 and filtered out to obtain the title compound (29.0 g) (colorless solid).

MS (ESI pos.) m/z: 236 [M+H]+

Reference Example 28

[1-(5-Fluoropyridin-2-yl)-1H-pyrazol-3-yl]methanol

[Formula 36]

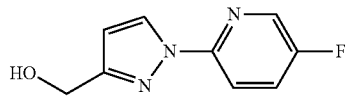

To a solution of ethyl-1-(5-fluoropyridin-2-yl)-1H-pyrazole-3-carboxylate obtained in Reference Example 27 (10.0 g, 42.5 mmol) in THF (50 mL), diisobutylaluminium hydride (a 1.01 mol/L toluene solution, 105.2 mL, 106.3 mmol) was added under cooling at −78° C., and after dropwise addition the resulting mixture was heated to 0° C. and stirred for 2 hours. An aqueous solution of potassium sodium tartrate (Rochelle salt) was added to the reaction mixture under ice-cooling, followed by extraction with EtOAc. The organic layer was washed with a saturated aqueous solution of sodium chloride, dried over MgSO4, then the drying agent was filtered off, and then the solvent was distilled off under reduced pressure to obtain the title compound (8.0 g) (colorless solid).

MS (ESI pos.) m/z: 194 [M+H]+

Reference Example 29

1-(5-Fluoropyridin-2-yl)-1H-pyrazole-3-carbaldehyde

[Formula 37]

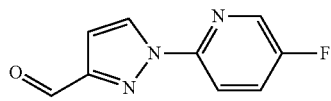

To a suspension of [1-(5-fluoropyridin-2-yl)-1H-pyrazol-3-yl]methanol obtained in Reference Example 28 (8.0 g, 34.0 mmol) in CHCl3 (100 mL), 85% manganese dioxide (29.6 g, 0.34 mol) was added, and the resulting mixture was stirred for 3 hours at 60° C. The reaction mixture was filtered through Celite®, the solid was washed with CHCl3, and the filtrate was concentrated under reduced pressure. The obtained residue was washed with diethyl ether, and filtered out to obtain the title compound (5.3 g) (light brown solid).

MS (ESI pos.) m/z: 192 [M+H]+

Reference Example 30

[1-(5-Fluoropyridin-2-yl)-1H-pyrazol-3-yl]acetaldehyde

[Formula 38]

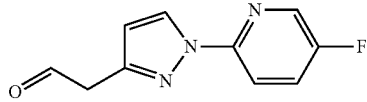

To a solution of methoxymethyltriphenyl phosphonium chloride (5.4 g, 15.7 mmol) in THF (50 mL), n-butyl lithium (a 2.6 mol/L hexane solution, 6.3 mL, 16.5 mmol) was added under cooling at −78° C., and the resulting mixture was stirred for 30 minutes. The reaction mixture was heated to 0° C., a solution of 1-(5-fluoropyridin-2-yl)-1H-pyrazole-3-carbaldehyde obtained in Reference Example 29 (1.5 g, 7.9 mmol) and hexamethylphosphoric triamide (0.5 mL) in THF (50 mL) was added thereto, the resulting mixture was stirred for 3 hours, then heated to room temperature and stirred for 15 hours. To the reaction mixture, EtOAc and a saturated aqueous solution of sodium chloride were added under cooling in an ice bath and stirred to separate the organic layer. The organic layer was dried over MgSO$_4$, then the drying agent was filtered off, and then the solvent was distilled off under reduced pressure to obtain a brown oil. To the obtained brown oil, an aqueous solution of hydrochloric acid (1.2 mol/L, 10 mL) was added, and the resulting mixture was heated to reflux and stirred for 2 hours. The reaction mixture was allowed to cool at room temperature, then water was added thereto, followed by extraction with EtOAc. The organic layer was washed with a saturated aqueous solution of sodium chloride, dried over MgSO$_4$, then the drying agent was filtered off, and then the solvent was distilled off under reduced pressure. The obtained residue was purified by column chromatography (HIP-Sil 25 g, hexane/EtOAc=80/20 to 20/80) to obtain the title compound (1.0 g) (light yellow oil).

MS (ESI pos.) m/z: 206 [M+H]$^+$

Reference Example 31

[2-(Hydroxymethyl)-1,3-oxazinan-3-yl][5-methyl-2-(2H-1,2,3-triazol-2-yl)phenyl]methanone

[Formula 39]

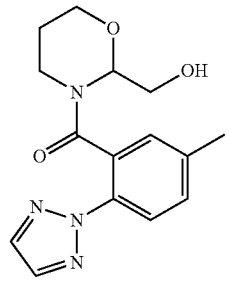

To a solution of (±)-[2-(hydroxymethyl)-1,3-oxazinan-3-yl][5-methyl-2-(2H-1,2,3-triazol-2-yl)phenyl]methanone obtained in Reference Example 4 (1.7 g, 5.7 mmol) in toluene (29 mL), pyridinium para-toluenesulfonate (0.14 g, 0.57 mol) and (S)-5-allyl-2-oxabicyclo[3.3.0]oct-8-ene (1.0 g, 6.9 mmol) were added and stirred at an oil bath temperature of 70° C. The reaction mixture was allowed to cool to room temperature, then a saturated aqueous solution of NaHCO$_3$ was added thereto, followed by extraction with EtOAc. The organic layer was washed with water and a saturated aqueous solution of sodium chloride, dried over Na$_2$SO$_4$, then the drying agent was filtered off, and then the solvent was distilled off under reduced pressure. The obtained residue was purified by column chromatography (RP-Sil 160 g, hexane/EtOAc=75/25 to 40/60) to obtain the low polar compound (0.89 g) of 2 kinds of diastereomer mixtures (colorless solid). To a solution of the obtained colorless solid diastereomer in MeOH (40 mL), tosyl acid monohydrate (0.075 g, 0.4 mmol) was added, and the resulting mixture was stirred for 15 hours at room temperature. A saturated aqueous solution of NaHCO$_3$ was added to the reaction mixture, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 10 g, hexane/EtOAc=75/25 to 0/100), (KP-NH 10 g, hexane/EtOAc=75/25 to 0/100) to obtain the title compound (0.58 g, 94% ee) (colorless oil). The optical purity was analyzed based on the racemic compound analysis conditions described earlier (condition 10, Rt$^1$=10.2 min, Rt$^2$=11.6 min) to obtain an excess of the compound having a short relative retention time (Rt$^1$=10.2 min).

MS (ESI pos.) m/z: 303 [M+H]$^+$

The title compound can be alternatively synthesized by a different method as follows.

To a solution of (±)-[2-(hydroxymethyl)-1,3-oxazinan-3-yl][5-methyl-2-(2H-1,2,3-triazol-2-yl)phenyl]methanone obtained in Reference Example 4 (1.0 mg, 0.0033 mmol), vinyl acetate (0.05 mL) and t-butyl methyl ether (1 mL), pig pancreas-derived lipase (9.5 mg, trade name Lipase from porcine pancreas Type II, manufactured by SIGMA Chemical Company) was added and stirred with shaking in a screw vial at 35° C. at 250 rpm for 24 hours. The reaction solution was filtered using EKICRODISK 13CR (manufactured by Pall Corporation). The filtrate was concentrated under reduced pressure, the obtained residue was HPLC analyzed under the above racemic compound analysis condition 10, and {3-[5-methyl-2-(2H-1,2,3-triazol-2-yl)benzoyl]-1,3-oxazinan-2-yl}methyl acetate (54.5%, 81.2% ee, compounds with longer retention time of Rt$^1$=7.3 min, Rt$^2$=8.9 min were excessive, colorless oil) and the title compound (45.5%, >99.9% ee, compounds with shorter retention time of Rt$^3$=10.2 min, Rt$^2$=11.6 min were excessive, colorless oil) were obtained.

MS (ESI pos.) m/z: 303 [M+H]$^+$

The title compound can be alternatively synthesized by a different method as follows.

To a solution of trifluorocopper methanesulfonate(II) (0.013 g, 0.040 mmol) and (R,R)-2,2'-isopropylidenebis(4-phenyl-2-oxazoline) (0.012 g, 0.040 mmol) in THF (1.5 mL), (±)-[2-(hydroxymethyl)-1,3-oxazinan-3-yl][5-methyl-2-(2H-1,2,3-triazol-2-yl)phenyl]methanone obtained in Reference Example 4 (0.36 g, 1.2 mmol), potassium carbonate (0.16 g, 1.2 mmol) and benzoyl chloride (0.069 g, 0.59 mmol) were added, and the resulting mixture was stirred for 3 hours at room temperature. Water was added to the reaction mixture, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 10 g, hexane/EtOAc=75/25 to 0/100) to obtain methyl{3-[5-methyl-2-(2H-1,2,3-triazol-2-yl)benzoyl]-1,3-oxazinan-2-yl}benzoate (0.16 g, 55% ee) (colorless oil). The optical purity was analyzed based on the racemic compound analysis conditions described earlier (condition 10, Rt$^1$=6.9 min, Rt$^2$=7.9 min) to obtain an excess of the compound having a short relative retention time (Rt$^1$=6.9 min). To a solution of the obtained colorless oil (0.020 g, 0.049 mmol) in MeOH (0.5 mL), potassium carbonate (0.010 g, 0.074 mmol) were added, and the resulting mixture was stirred for 2 hours at room temperature. Water was added to the reaction mixture, followed by extraction with EtOAc. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 10 g, hexane/EtOAc=75/25 to 0/100) to obtain the title compound (0.011 g, 55% ee) (colorless oil). The optical purity was analyzed based on the racemic compound analysis conditions described earlier (condition 10, Rt$^1$=10.2 min, Rt$^2$=11.6 min) to obtain an excess of the compound having a short relative retention time (Rt$^1$=10.2 min).

MS (ESI pos.) m/z: 303 [M+H]$^+$

Reference Example 32

[2-(Chloromethyl)-1,3-oxazinan-3-yl][5-methyl-2-(2H-1,2,3-triazol-2-yl)phenyl]methanone

[Formula 40]

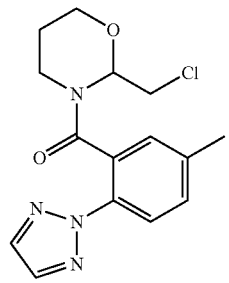

To a solution of [2-(hydroxymethyl)-1,3-oxazinan-3-yl][5-methyl-2-(2H-1,2,3-triazol-2-yl)phenyl]methanone obtained in Reference Example 31 (1.8 g, 5.8 mmol, 86.3% ee) and TEA (1.2 mL, 8.7 mmol) in CHCl$_3$ (30 mL), MsCl (0.54 mL, 7.0 mmol) was added under cooling with ice water. The resulting mixture was heated to room temperature and then stirred for 3 hours. Water was added to the reaction mixture, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 10 g, hexane/EtOAc=88/12 to 0/100). EtOAc (10 mL) was added to the obtained residue, the resulting mixture was stirred for 30 minutes under cooling in an ice bath, and the solid was filtered out to obtain the title compound (0.81 g, 84.2% ee) (colorless solid). The optical purity was analyzed based on the racemic compound analysis conditions described earlier (condition 12, Rt$^1$=7.7 min, Rt$^2$=11.9 min) to obtain the compound containing an excess of the compound having a long relative retention time (Rt$^2$=11.9 min).

MS (ESI pos.) m/z: 321 [M+H]$^+$

Reference Example 33

Ethyl(2RS,5SR)-5-methyl-3-[5-methyl-2-(2H-1,2,3-triazol-2-yl)benzoyl]-1,3-oxazinane-2-carboxylate

[Formula 41]

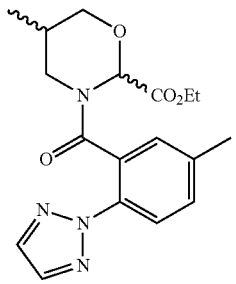

To a solution of ethyl(2RS,5RS)-5-methyl-3-[5-methyl-2-(2H-1,2,3-triazol-2-yl)benzoyl]-1,3-oxazinane-2-carboxylate obtained in Reference Example 18 (2.1 g, 6.0 mmol) in ethanol (60 mL), potassium carbonate (7.4 g, 53.8 mmol) was added, and the resulting mixture was stirred for 7 hours at 75° C. The reaction mixture was allowed to cool to room temperature, then water was added thereto, and the solvent was concentrated under reduced pressure, followed by extraction with EtOAc. The organic layer was washed with water and a saturated aqueous solution of sodium chloride, dried over Na$_2$SO$_4$, then the drying agent was filtered off, and then the solvent was distilled off under reduced pressure. The obtained residue was purified by column chromatography (HP-Sil 120 g, hexane/EtOAc=90/10 to 30/70) to obtain the title compound (0.72 g) (colorless oil).

MS (ESI pos.) m/z: 359 [M+H]$^+$

Reference Example 34

[(2RS,5SR)-2-(Hydroxymethyl)-5-methyl-1,3-oxazinan-3-yl][5-methyl-2-(2H-1,2,3-triazol-2-yl)phenyl]methanone

[Formula 42]

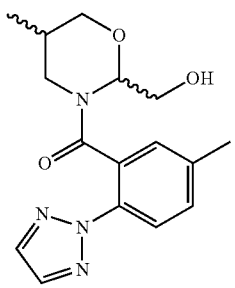

By using ethyl(2RS,5SR)-5-methyl-3-[5-methyl-2-(2H-1,2,3-triazol-2-yl)benzoyl]-1,3-oxazinane-2-carboxylate obtained in Reference Example 33 (0.72 g, 2.0 mmol) as the raw material, the same procedure as in Reference Example 2 was carried out to obtain the title compound (0.59 g) (colorless oil).

MS (ESI pos.) m/z: 317 [M+H]$^+$

Reference Example 35

(2RS,5SR)-[2-(chloromethyl)-5-methyl-1,3-oxazinan-3-yl][5-methyl-2-(2H-1,2,3-triazol-2-yl)phenyl]methanone

[Formula 43]

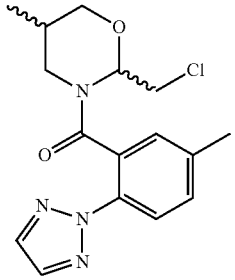

By using [(2RS,5SR)-2-(hydroxymethyl)-5-methyl-1,3-oxazinan-3-yl][5-methyl-2-(2H-1,2,3-triazol-2-yl)phenyl]methanone obtained in Reference Example 34 (0.59 g, 1.9 mmol) as the raw material, the same procedure as in Reference Example 32 was carried out to obtain the title compound (0.52 g) (colorless oil).

MS (ESI pos.) m/z: 335 [M+H]$^+$

Example 1

(−)-(2-{[3-(5-Fluoropyridin-2-yl)-1H-pyrazol-1-yl]methyl}-1,3-oxazolidin-3-yl)[5-methyl-2-(2H-1,2,3-triazol-2-yl)phenyl]methanone

[Formula 44]

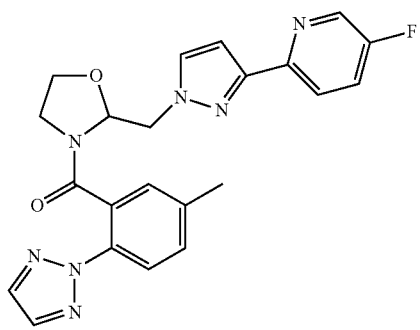 [SMILES: Cc1ccc(-n2nccn2)c(C(=O)N2CCOC2Cn2cc(-c3ccc(F)cn3)cn2)c1]

To a solution of [2-(hydroxymethyl)-1,3-oxazolidin-3-yl][5-methyl-2-(2H-1,2,3-triazol-2-yl)phenyl]methanone obtained in Reference Example 2 (1.7 g, 5.9 mmol) and TEA (1.2 mL, 8.8 mmol) in CHCl$_3$ (30 mL), MsCl (0.55 mL, 7.1 mmol) was added under cooling with ice water, and the resulting mixture was stirred for 1 hour. Water was added to the reaction mixture under cooling with ice water, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. The obtained residue was purified by column chromatography (HP-Sil 50 g, hexane/EtOAc=88/12 to 0/100) to obtain methyl{3-[5-methyl-2-(2H-1,2,3-triazol-2-yl)benzoyl]-1,3-oxazolidin-2-yl}methanesulfonate (pale yellow oil). 5-Fluoro-2-(1H-pyrazol-3-yl)pyridine (1.3 g, 8.1 mmol) and Cs$_2$CO$_3$ (4.8 g, 14.7 mmol) were added to a solution of the obtained pale yellow oil in DMF (30 mL), and the resulting mixture was stirred for 24 hours at an oil bath temperature of 90° C. The reaction mixture was allowed to cool to room temperature, then water was added thereto, followed by extraction with EtOAc, and the solvent was distilled off under reduced pressure. The obtained residue was purified by column chromatography (HP-Sil 150 g, hexane/EtOAc=88/12 to 0/100) to obtain the racemic mixture of title compound (1.2 g) (pale yellow oil). The obtained racemic mixture was divided using a semi-preparative column based on the racemic compound analysis conditions described earlier (condition 1, Rt$^1$=3.6 min, Rt$^2$=7.0 min) to obtain the title compound (0.39 g) (colorless solid) having a short relative retention time (Rt$^1$=3.6 min).

LCMS retention time: 0.90 min.
MS (ESI pos.) m/z: 434 [M+H]$^+$
$[\alpha]_D^{25}$=−71.0 (c=0.0994, CHCl$_3$)

Examples 2 to 4 were obtained by the same procedure as in Example 1. The structural formula, the names, LCMS data and specific optical rotation of the obtained compounds are shown in Table 2.

TABLE 2

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 2 | | (−)-(2-[[4-(5-fluoropyridin-2-yl)-1H-pyrazol-1-yl]-methyl]-1,3-oxazolidin-3-yl)[5-methyl-2-(2H-1,2,3-triazol-2-yl)phenyl]methanone | 434 (M + H)$^+$ | 0.86 | Condition 2 Rt$^1$ = 13.4 | $[\alpha]_D^{22}$ = −92.0 (c = 0.105, CHCl$_3$) |
| Example 3 | | (−)-(2-[[3-(5-fluoropyridin-2-yl)-1H-pyrazol-1-yl]-methyl]-1,3-oxazinan-3-yl)[5-methyl-2-(2H-1,2,3-triazol-2-yl)phenyl]methanone | 448 (M + H)$^+$ | 0.89 | Condition 9 Rt$^1$ = 4.3 | $[\alpha]_D^{27}$ = −33.2 (c = 0.102, CHCl$_3$) |

TABLE 2-continued

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 4 | 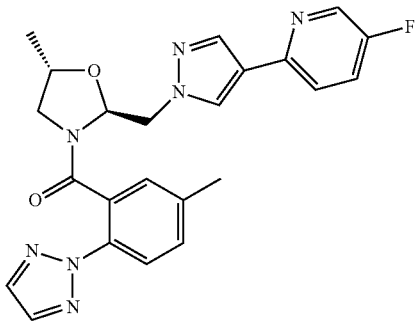 | (−)-(2-[[4-(5-fluoropyridin-2-yl)-1H-pyrazol-1-yl]-methyl]-1,3-oxazinan-3-yl)[5-methyl-2-(2H-1,2,3-triazol-2-yl)phenyl]methanone | 448 (M + H)+ | 0.85 | Condition 3 Rt[1] = 7.4 | $[\alpha]_D^{25}$ = −31.8 (c = 0.0998, CHCl$_3$) |

Example 5

(−)-[(2S,5S)-2-{[4-(5-Fluoropyridin-2-yl)-1H-pyrazol-1-yl]methyl}-5-methyl-1,3-oxazolidin-3-yl][5-methyl-2-(2H-1,2,3-triazol-2-yl)phenyl]methanone

[Formula 45]

By using ethyl(2RS,5S)-5-methyl-3-[5-methyl-2-(2H-1,2,3-triazol-2-yl)benzoyl]-1,3-oxazolidine-2-carboxylate obtained in Reference Example 5 (0.11 g, 0.33 mmol) as the raw material, the same procedure as in Reference Example 2 was carried out to obtain the diastereomer mixture of [2-(hydroxymethyl)-5-methyl-1,3-oxazolidin-3-yl][5-methyl-2-(2H-1,2,3-triazol-2-yl)phenyl]methanone (colorless oil). The obtained diastereomer mixture was purified by thin layer chromatography (1 mm, hexane/EtOAc=50/50) to obtain [(2S,5S)-2-(hydroxymethyl)-5-methyl-1,3-oxazolidin-3-yl][5-methyl-2-(2H-1,2,3-triazol-2-yl)phenyl]methanone (colorless oil). To a solution of the obtained [(2S,5S)-2-(hydroxymethyl)-5-methyl-1,3-oxazolidin-3-yl][5-methyl-2-(2H-1,2,3-triazol-2-yl)phenyl]methanone (30.2 mg, 0.10 mmol) and TEA (0.021 mL, 0.15 mmol) in CHCl$_3$ (0.8 mL), MsCl (0.011 mL, 0.15 mmol) were added under cooling with ice water and the resulting mixture was stirred for 1 hour. Water was added to the reaction mixture under cooling with ice water, followed by extraction with CHCl$_3$. The organic layer was washed with a saturated aqueous solution of sodium chloride, dried over Na$_2$SO$_4$, then the drying agent was filtered off, and then the solvent was distilled off under reduced pressure. 5-Fluoro-2-(1H-pyrazol-4-yl)pyridine (0.033 g, 0.20 mmol) and Cs$_2$CO$_3$ (0.065 g, 0.20 mmol) were added to a solution of the obtained residue (0.5 mL). The resulting mixture was reacted for 1 hour at 120° C. under irradiation of microwave. The reaction mixture was allowed to cool, water was added thereto, followed by extraction with CHCl$_3$, the extract was passed through an ISOLUTE Phase Separator, and the solvent was distilled off under reduced pressure. The obtained residue was purified by HPLC to obtain the title compound (0.020 g) (colorless oil).

LCMS retention time: 0.92 min.
MS (ESI pos.) m/z: 448 [M+H]+
$[\alpha]_D^{25}$=−80.4 (c=0.0828, CHCl$_3$)

Examples 6 to 10 were obtained by the same procedure as in Example 5. The structural formula, the names, LCMS data and specific optical rotation of the obtained compounds are shown in Table 3.

TABLE 3

| Example No. | Structural formula | Compound name | MS (ESI pos.) m/z | LCMS retention time (min) | Specific optical rotation |
|---|---|---|---|---|---|
| Example 6 | | (−)-[(2S,5R)-2-[[4-(5-fluoropyridin-2-yl)-1H-pyrazol-1-yl]methyl]-5-methyl-1,3-oxazolidin-3-yl][5-methyl-2-(2H-1,2,3-triazol-2-yl)phenyl]methanone | 448 (M + H)+ | 0.94 | $[\alpha]_D^{25}$ = −130 (c = 0.074, CHCl$_3$) |

TABLE 3-continued

| Example No. | Structural formula | Compound name | MS (ESI pos.) m/z | LCMS retention time (min) | Specific optical rotation |
|---|---|---|---|---|---|
| Example 7 | | [(2S,4R)-2-[[3-(5-fluoropyridin-2-yl)-1H-pyrazol-1-yl]-methyl]-4-methyl-1,3-oxazolidin-3-yl][5-methyl-2-(2H-1,2,3-triazol-2-yl)phenyl]methanone | 448 (M + H)+ | 0.95 | — |
| Example 8 | | [(2S,4R)-2-[[4-(5-fluoropyridin-2-yl)-1H-pyrazol-1-yl]-methyl]-4-methyl-1,3-oxazolidin-3-yl][5-methyl-2-(2H-1,2,3-triazol-2-yl)phenyl]methanone | 448 (M + H)+ | 0.91 | — |
| Example 9 | | (−)-[(2S,4S)-2-[[3-(5-fluoropyridin-2-yl)-1H-pyrazol-1-yl]-methyl]-4-methyl-1,3-oxazolidin-3-yl][5-methyl-2-(2H-1,2,3-triazol-2-yl)phenyl]methanone | 448 (M + H)+ | 0.98 | $[\alpha]_D^{25} = -23.2$ (c = 0.10, CHCl$_3$) |
| Example 10 | | (−)-[(2S,4S)-2-[[4-(5-fluoropyridin-2-yl)-1H-pyrazol-1-yl]methyl]-4-methyl-1,3-oxazolidin-3-yl][5-methyl-2-(2H-1,2,3-triazol-2-yl)phenyl]methanone | 448 (M + H)+ | 0.94 | $[\alpha]_D^{25} = -22.8$ (c = 0.095, CHCl$_3$) |

Example 11

(±)-(2-{[3-(5-Fluoropyridin-2-yl)-1H-pyrazol-1-yl]methyl}-1,3-oxazolidin-3-yl)[2-(2H-1,2,3-triazol-2-yl)phenyl]methanone

[Formula 46]

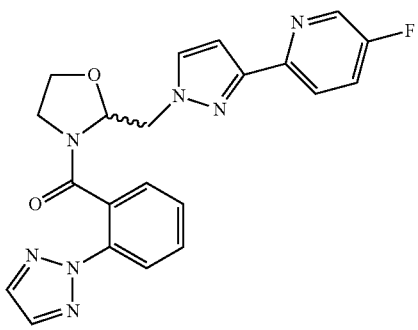

To a solution of 2-[1-(2,2-diethoxyethyl)-1H-pyrazol-3-yl]-5-fluoropyridine obtained in Reference Example 12 (4.0 g, 14.3 mmol) in CHCl$_3$ (72 mL), TFA (6.4 mL, 85.9 mmol) was added, and the resulting mixture was stirred for 6 hours at 35° C. TFA (6.4 mL, 85.9 mmol) was further added thereto, and the mixture was stirred for 3 hours at 35° C. The reaction mixture was allowed to cool to room temperature, then an aqueous solution of NaHCO$_3$ was added to the reaction mixture, followed by extraction with CHCl$_3$. The organic layer was washed with a saturated aqueous solution of sodium chloride, dried over MgSO$_4$, and then the drying agent was filtered off. The solvent was distilled off under reduced pressure to obtain [3-(5-fluoropyridin-2-yl)-1H-pyrazol-1-yl]acetaldehyde (colorless oil). To a solution of [3-(5-fluoropyridin-2-yl)-1H-pyrazol-1-yl]acetaldehyde in CHCl$_3$ (36 mL), activated molecular sieve 4 A (29 g) and 2-aminoethanol (1.1 mL, 14.3 mmol) were added, and the resulting mixture was stirred for 48 hours at room temperature. The molecular sieve 4 A was filtered off through Celite®, and then the solvent was distilled off under reduced pressure to obtain a colorless oil. To a solution of the obtained colorless oil (0.10 g, 0.40 mmol) and 2-(2H-1,2,3-triazol-2-yl)benzoic acid (76 mg, 0.40 mmol) in DMF (0.4 mL), DIPEA (0.21 mL, 1.2 mmol) and HATU (0.16 g, 0.48 mmol) were added, and the resulting mixture was stirred for 48 hours at room temperature. The reaction mixture was purified by HPLC to obtain the title compound (40.8 mg) (colorless solid).

LCMS retention time: 0.83 min.
MS (ESI pos.) m/z: 420 [M+H]+

Examples 12 to 38 were obtained by the same procedure as in Example 11. Examples 26 to 32 and Examples 34 to 38 were optically divided by the same procedure as in Example 1. The structural formula, the names, LCMS data and specific optical rotation of the obtained compounds are shown in Tables 4-1 to 4-4.

TABLE 4-1

| Example No. | Structural formula | Compound name | MS (ESI pos.) m/z | LCMS retention time (min) |
|---|---|---|---|---|
| Example 12 | | (±)-(2-[[3-(5-fluoropyridin-2-yl)-1H-pyrazol-1-yl]methyl]-1,3-oxazolidin-3-yl)[5-fluoro-2-(2H-1,2,3-triazol-2-yl)phenyl]methanone | 438 (M + H)+ | 0.87 |
| Example 13 | | (±)-(2-[[3-(5-fluoropyridin-2-yl)-1H-pyrazol-1-yl]methyl]-1,3-oxazolidin-3-yl)[6-methyl-3-(2H-1,2,3-triazol-2-yl)pyridin-2-yl]methanone | 435 (M + H)+ | 0.78 |
| Example 14 | | (±)-2-[[3-(5-fluoropyridin-2-yl)-1H-pyrazol-1-yl]methyl]-1,3-oxazolidin-3-yl][5-methyl-2-(pyrimidin-2-yl)phenyl]methanone | 445 (M + H)+ | 0.88 |
| Example 15 | | (±)-(2-[[3-(5-fluoropyridin-2-yl)-1H-pyrazol-1-yl]methyl]-1,3-oxazolidin-3-yl)[2-(pyrimidin-2-yl)phenyl]methanone | 431 (M + H)+ | 0.81 |

TABLE 4-1-continued

| Example No. | Structural formula | Compound name | MS (ESI pos.) m/z | LCMS retention time (min) |
|---|---|---|---|---|
| Example 16 | | (±)-(2-[[3-(5-fluoropyridin-2-yl)-1H-pyrazol-1-yl]methyl]-1,3-oxazolidin-3-yl)[5-fluoro-2-(pyrimidin-2-yl)phenyl]methanone | 449 (M + H)+ | 0.85 |
| Example 17 | | (±)-(2-[[3-(4-fluorophenyl)-1H-pyrazol-1-yl]methyl]-1,3-oxazolidin-3-yl)[5-methyl-2-2H-1,2,3-triazol-2-yl)phenyl]methanone | 433 (M + H)+ | 1.04 |
| Example 18 | | (±)-(2-[[3-(4-fluorophenyl)-1H-pyrazol-1-yl]methyl]-1,3-oxazolidin-3-yl)[2-(2H-1,2,3-triazol-2-yl)phenyl]methanone | 419 (M + H)+ | 0.98 |

TABLE 4-2

| Example No. | Structural formula | Compound name | MS (ESI pos.) m/z | LCMS retention time (min) |
|---|---|---|---|---|
| Example 19 | | (±)-(2-[[3-(4-fluorophenyl)-1H-pyrazol-1-yl]methyl]-1,3-oxazolidin-3-yl)[5-fluoro-2-(2H-1,2,3-triazol-2-yl)phenyl]methanone | 437 (M + H)+ | 1.01 |

TABLE 4-2-continued

| Example No. | Structural formula | Compound name | MS (ESI pos.) m/z | LCMS retention time (min) |
| --- | --- | --- | --- | --- |
| Example 20 | | (±)-(2-[[3-(4-fluorophenyl)-1H-pyrazol-1-yl]methyl]-1,3-oxazolidin-3-yl)[5-methyl-2-(pyrimidin-2-yl)phenyl]methanone | 444 (M + H)+ | 1.01 |
| Example 21 | | (±)-(2-[[3-(4-fluorophenyl)-1H-pyrazol-1-yl]methyl]-1,3-oxazolidin-3-yl)[5-methyl-2-(pyrimidin-2-yl)phenyl]methanone | 448 (M + H)+ | 0.99 |
| Example 22 | | (±)-(2-[[4-(4-fluorophenyl)-1H-pyrazol-1-yl]methyl]-1,3-oxazolidin-3-yl)[5-methyl-2-(2H-1,2,3-triazol-2-yl)phenyl]methanone | 433 (M + H)+ | 1.00 |
| Example 23 | | (±)-(2-[[4-(4-fluorophenyl)-1H-pyrazol-1-yl]methyl]-1,3-oxazolidin-3-yl)[6-methyl-3-(2H-1,2,3-triazol-2-yl)pyridin-2-yl]methanone | 434 (M + H)+ | 0.90 |
| Example 24 | | (±)-(2-[[4-(4-fluorophenyl)-1H-pyrazol-1-yl]methyl]-1,3-oxazolidin-3-yl)[5-methyl-2-(pyrimidin-2-yl)phenyl]methanone | 444 (M + H)+ | 0.97 |

TABLE 4-2-continued

| Example No. | Structural formula | Compound name | MS (ESI pos.) m/z | LCMS retention time (min) |
|---|---|---|---|---|
| Example 25 | | (±)-(2-[[4-(4-fluorophenyl)-1H-pyrazol-1-yl]methyl]-1,3-oxazolidin-3-yl)[5-fluoro-2-(pyrimidin-2-yl)phenyl]methanone | 448 (M + H)+ | 0.96 |
| Example 33 | | (±)-(2-[[5-(5-fluoropyridin-2-yl)-1,2,4-oxadiazol-3-yl]methyl]-1,3-oxazinan-3-yl)[5-methyl-2-(pyrimidin-2-yl)phenyl]methanone | 461 (M + H)+ | 0.79 |

TABLE 4-3

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 26 | | (−)-(2-[[3-(4-fluorophenyl)-1H-pyrazol-1-yl]methyl]-1,3-oxazolidin-3-yl)[6-methyl-3-(2H-1,2,3-triazol-2-yl)pyridin-2-yl]methanone | 434 (M + H)+ | 0.94 | Condition 1 $Rt^1$ = 3.8 | $[\alpha]_D^{27}$ = −156.4 (c = 0.0954, CHCl$_3$) |
| Example 27 | | (−)-(2-[[3-(4-fluorophenyl)-1H-pyrazol-1-yl]methyl]-1,3-oxazinan-3-yl)[6-methyl-3-(2H-1,2,3-triazol-2-yl)pyridin-2-yl]methanone | 448 (M + H)+ | 0.94 | Condition 1 $Rt^1$ = 4.3 | $[\alpha]_D^{27}$ = −71.0 (c = 0.0230, CHCl$_3$) |
| Example 28 | | (−)-(2-[[3-(4-fluorophenyl)-1H-pyrazol-1-yl]methyl]-1,3-oxazinan-3-yl)[6-methyl-3-(pyrimidin-2-yl)pyridin-2-yl]methanone | 459 (M + H)+ | 0.91 | Condition 1 $Rt^1$ = 4.5 | $[\alpha]_D^{27}$ = −25.1 (c = 0.0666, CHCl$_3$) |

TABLE 4-3-continued

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 29 | | (−)-(2-[[3-(5-fluoropyridin-2-yl)-1H-pyrazol-1-yl]methyl]-1,3-oxazinan-3-yl)[5-fluoro-2-(2H-1,2,3-triazol-2-yl)phenyl]methanone | 452 (M + H)$^+$ | 0.87 | Condition 1 Rt$^1$ = 4.5 | $[\alpha]_D^{27}$ = −36.3 (c = 0.0560, CHCl$_3$) |
| Example 30 | | (−)-(2-[[3-(5-fluoropyridin-2-yl)-1H-pyrazol-1-yl]methyl]-1,3-oxazinan-3-yl)[5-fluoro-2-(2H-1,2,3-triazol-2-yl)phenyl]methanone | 459 (M + H)$^+$ | 0.86 | Condition 1 Rt$^1$ = 4.2 | $[\alpha]_D^{28}$ = −32.5 (c = 0.0684, CHCl$_3$) |
| Example 31 | | (−)-(2-[[4-(4-fluorophenyl)-1H-pyrazol-1-yl]methyl]-1,3-oxazinan-3-yl)[6-methyl-3-(2H-1,2,3-triazol-2-yl)pyridin-2-yl]methanone | 448 (M + H)$^+$ | 0.91 | Condition 3 Rt$^1$ = 7.0 | $[\alpha]_D^{27}$ = −19.8 (c = 0.116, CHCl$_3$) |
| Example 32 | | (−)-(2-[[4-(4-fluorophenyl)-1H-pyrazol-1-yl]methyl]-1,3-oxazinan-3-yl)[6-methyl-3-(pyrimidin-2-yl)pyridin-2-yl]methanone | 459 (M + H)$^+$ | 0.88 | Condition 3 Rt$^1$ = 7.5 | $[\alpha]_D^{27}$ = −10.9 (c = 0.101, CHCl$_3$) |

TABLE 4-4

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 34 | | (−)-[2-[[3-(5-fluoropyridin-2-yl)-1H-pyrazol-1-yl]methyl]-1,3-oxazinan-3-yl][5-fluoro-2-(pyrimidin-2-yl)phenyl]methanone | 463 (M + H)$^+$ | 0.85 | Condition 4 Rt$^1$ = 3.7 | $[\alpha]_D^{23}$ = −36.6 (c = 0.0898, CHCl$_3$) |
| Example 35 | | (−)-[2-[[4-(4-fluorophenyl)-1H-pyrazol-1-yl]methyl]-1,3-oxazinan-3-yl][5-methyl-2-(2H-1,2,3-triazol-2-yl)phenyl]methanone | 447 (M + H)$^+$ | 0.99 | Condition 5 Rt$^1$ = 5.9 | $[\alpha]_D^{23}$ = −30.6 (c = 0.0968, CHCl$_3$) |

TABLE 4-4-continued

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 36 | | (−)-[2-[[5-(5-fluoropyridin-2-yl)-1,2,4-oxadiazol-3-yl]methyl]-1,3-oxazinan-3-yl][5-methyl-2-(2H-1,2,3-triazol-2-yl)phenyl]methanone | 450 (M + H)$^+$ | 0.89 | Condition 6 Rt$^2$ = 11.8 | [α]$_D^{23}$ = −31.4 (c = 0.0786, CHCl$_3$) |
| Example 37 | | (−)-[2-[[5-(4-fluorophenyl)-1,2,4-oxadiazol-3-yl]methyl]-1,3-oxazinan-3-yl][5-methyl-2-(2H-1,2,3-triazol-2-yl)phenyl]methanone | 449 (M + H)$^+$ | 1.0 | Condition 6 Rt$^2$ = 13.7 | [α]$_D^{23}$ = −35.8 (c = 0.193, CHCl$_3$) |
| Example 38 | | (−)-[2-[[5-(4-fluorophenyl)-1,2,4-oxadiazol-3-yl]methyl]-1,3-oxazinan-3-yl][6-methyl-3-(2H-1,2,3-triazol-2-yl)pyridin-2-yl]methanone | 450 (M + H)$^+$ | 0.93 | Condition 6 Rt$^2$ = 12.8 | [α]$_D^{23}$ = −4.91 (c = 0.101, CHCl$_3$) |

Example 39

[(2S,4S)-2-{[4-(5-Fluoropyridin-2-yl)-1H-pyrazol-1-yl]methyl}-4-methyl-1,3-oxazinan-3-yl][5-methyl-2-(2H-1,2,3-triazol-2-yl)phenyl]methanone

[Formula 47]

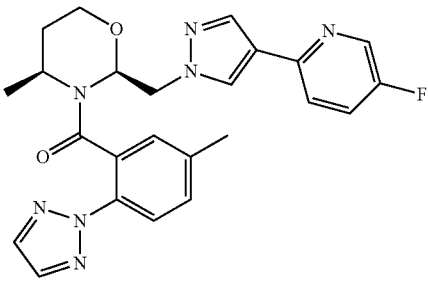

To a solution of [(2S,4S)-2-(hydroxymethyl)-4-methyl-1,3-oxazinan-3-yl][5-methyl-2-(2H-1,2,3-triazol-2-yl)phenyl]methanone obtained in Reference Example 17 (0.070 g, 0.22 mmol) in toluene (1 mL), 5-fluoro-2-(1H-pyrazol-4-yl)pyridine obtained in Reference Example 11 (0.040 g, 0.24 mmol) and cyanomethylene tributylphosphorane (0.087 mL, 0.33 mmol) were added, and the resulting mixture was stirred with heating for 3 hours at 100° C. The solvent was distilled off under reduced pressure, and the obtained residue was purified by column chromatography (KP-NH 12 g, hexane/EtOAc=80/20 to 0/100) (HP-Sil 10 g, hexane/EtOAc=80/20 to 0/100) to obtain the title compound (0.11 g) (colorless oil).
LCMS retention time: 0.96 min.
MS (ESI pos.) m/z: 462 [M+H]$^+$

Example 40

(−)-[(2S*,5S*)-2-{[4-(5-Fluoropyridin-2-yl)-1H-pyrazol-1-yl]methyl}-5-methyl-1,3-oxazinan-3-yl][5-methyl-2-(2H-1,2,3-triazol-2-yl)phenyl]methanone

[Formula 48]

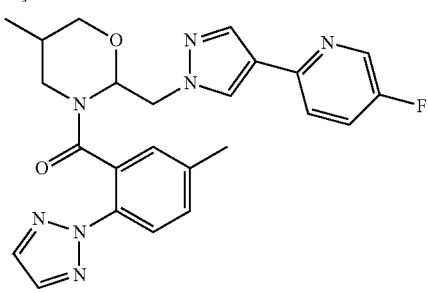

By using ethyl (2RS,5RS)-5-methyl-3-[5-methyl-2-(2H-1,2,3-triazol-2-yl)benzoyl]-1,3-oxazinane-2-carboxylate obtained in Reference Example 18 (0.13 g, 0.36 mmol) as the raw material, the same procedure as in Reference Example 2 was carried out to obtain [(2RS,5RS)-2-(hydroxymethyl)-5- methyl-1,3-oxazinan-3-yl][5-methyl-2-(2H-1,2,3-triazol-2-yl)phenyl]methanone (0.098 g) (colorless oil). By using the obtained colorless oil (0.098 g, 0.31 mmol) and 5-fluoro-2-(1H-pyrazol-4-yl)pyridine obtained in Reference Example 11 (0.056 g, 0.34 mmol) as the raw materials, the same procedure as in Example 39 was carried out to obtain the racemic mixture of title compound (0.11 g). The obtained racemic mixture was divided using a semi-preparative column based on the racemic compound analysis conditions described earlier (condition 7, $Rt^1$=4.3 min, $Rt^2$=4.8 min) to obtain the title compound (0.44 g) having a short relative retention time ($Rt^1$=4.3 min) (colorless oil).

LCMS retention time: 0.94 min.
MS (ESI pos.) m/z: 462 [M+H]+
$[\alpha]_D^{23}$=−44.1 (c=0.0704, CHCl$_3$)

Example 41

(−)-[2-{[3-(4-Fluorophenyl)-1H-pyrazol-1-yl]methyl}-1,3-oxazinan-3-yl][5-methyl-2-(pyrimidin-2-yl)phenyl]methanone

[Formula 49]

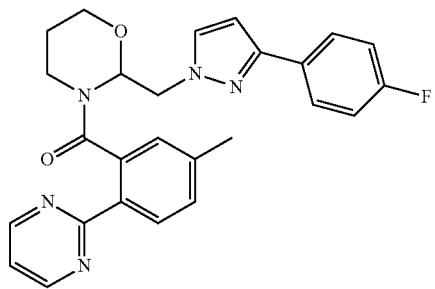

To a solution of (±)-(2-{[3-(4-fluorophenyl)-1H-pyrazol-1-yl]methyl}-1,3-oxazinan-3-yl)(2-iodo-5-methylphenyl)methanone obtained in Reference Example 23 (0.19 g, 0.38 mmol) and (tributylstannanyl)pyrimidine (0.15 mL, 0.46 mmol) in toluene (4 mL), Pd(PPh$_3$)$_4$ (0.044 g, 0.04 mmol), copper iodide (0.0070 g, 0.040 mmol) and cesium fluoride (0.12 g, 0.76 mmol) were added, and the resulting mixture was stirred with heating for 0.5 hours at 130° C. under irradiation of microwave. An aqueous solution of potassium fluoride was added to the reaction mixture, followed by extraction with CHCl$_3$. The organic layer was washed with an aqueous solution of potassium fluoride, water and a saturated aqueous solution of sodium chloride. The organic layer was dried over Na$_2$SO$_4$, the drying agent was filtered off, and then concentrated under reduced pressure. The obtained residue was purified by column chromatography (HP-Sil 10 g, hexane/EtOAc=80/20 to 0/100) (KP-NH 12 g, hexane/EtOAc=80/20 to 0/100) to obtain the racemic mixture of title compound (0.099 g) (colorless oil). The obtained racemic mixture was divided using a semi-preparative column based on the racemic compound analysis conditions described earlier (condition 4, $Rt^1$=3.9 min, $Rt^2$=13.7 min) to obtain the title compound (0.036 g) having a short relative retention time ($Rt^1$=3.9 min) (colorless oil).

LCMS retention time: 1.0 min.
MS (ESI pos.) m/z: 458 [M+H]+
$[\alpha]_D^{23}$=−34.1 (c=0.0914, CHCl$_3$)

Examples 42 to 44 were obtained by the same procedure as in Example 41. The structural formula, the names, LCMS data and specific optical rotation of Examples 42 to 44 are shown in Table 5.

TABLE 5

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 42 | | (±)-[2-[[1-(5-fluoropyridin-2-yl)-1H-pyrazol-4-yl]methyl]-1,3-oxazinan-3-yl][5-methyl-2-(pyrimidin-2-yl)phenyl]methanone | 459 (M + H)+ | 0.94 | — | — |
| Example 43 | | (−)-[2-[[4-(4-fluorophenyl)-1H-pyrazol-1-yl]methyl]-1,3-oxazinan-3-yl][5-methyl-2-(pyrimidin-2-yl)phenyl]methanone | 458 (M + H)+ | 0.97 | Condition 8 $Rt^1$ = 5.6 | $[\alpha]_D^{23}$ = −28.2 (c = 0.0504, CHCl$_3$) |

TABLE 5-continued

| Example No. | Structural formula | Compound name | MS (ESI pos.) m/z | LCMS retention time (min) | Racemic compound analysis condition Retention time (min) | Specific optical rotation |
|---|---|---|---|---|---|---|
| Example 44 | 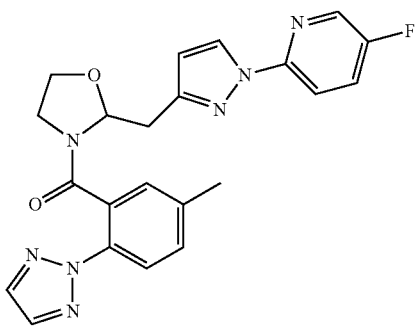 | (−)-[2-[[1-(5-fluoropyridin-2-yl)-1H-pyrazol-4-yl]methyl]-1,3-oxazinan-3-yl][5-fluoro-2-(pyrimidin-2-yl)phenyl]methanone | 463 (M + H)+ | 0.92 | Condition 5 Rt¹ = 19.5 | $[\alpha]_D^{23} = -16.6$ (c = 0.123, CHCl₃) |

Example 45

(−)-[2-{[1-(5-Fluoropyridin-2-yl)-1H-pyrazol-3-yl]methyl}-1,3-oxazolidin-3-yl][5-methyl-2-(2H-1,2,3-triazol-2-yl)phenyl]methanone

[Formula 50]

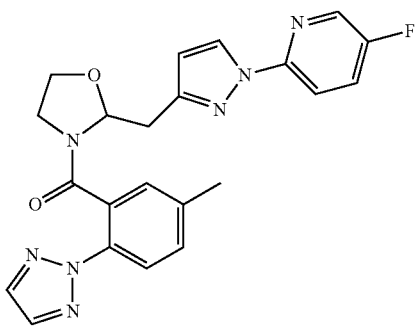

By using [1-(5-fluoropyridin-2-yl)-1H-pyrazol-3-yl]acetaldehyde obtained in Reference Example 30 (0.80 g, 3.9 mmol), the same procedure as in Example 11 was carried out to obtain the racemic mixture (0.063 g) (light yellow solid). The obtained racemic mixture was divided using a semi-preparative column based on the racemic compound analysis condition described earlier (condition 9, Rt¹=4.6 min, Rt²=13.8 min) to obtain the title compound (0.017 g) (colorless solid) having a short relative retention time (Rt¹=4.6 min).

LCMS retention time: 1.0 min.
MS (ESI pos.) m/z: 434 [M+H]+
$[\alpha]_D^{23}$=−104.0 (c=0.0566, CHCl₃)

Example 46

(−)-[2-{[1-(5-Fluoropyridin-2-yl)-1H-pyrazol-4-yl]methyl}-1,3-oxazolidin-3-yl][5-methyl-2-(2H-1,2,3-triazol-2-yl)phenyl]methanone

[Formula 51]

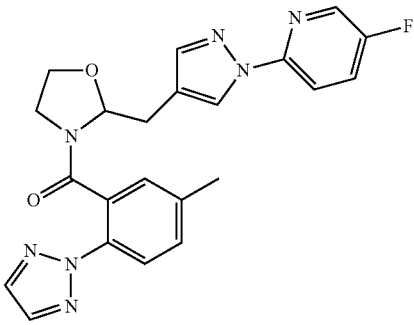

By using 2-[1-(5-fluoropyridin-2-yl)-1H-pyrazol-4-yl]ethanol obtained in Reference Example 22 (0.30 g, 1.5 mmol) as the raw material, the same procedure as in Reference Example 25 was carried out to obtain the racemic mixture of title compound (0.039 g) (colorless oil). The obtained racemic mixture was divided using a semi-preparative column based on the racemic compound analysis conditions described earlier (condition 2, Rt¹=16.3 min, Rt²=19.2 min) to obtain the title compound (0.0076 g) (colorless solid) having a short relative retention time (Rt¹=16.3 min).

LCMS retention time: 0.97 min.
MS (ESI pos.) m/z: 434 [M+H]+
$[\alpha]_D^{23}$=−80.9 (c=0.0478, CHCl₃)

Example 47

(−)-[2-{[1-(5-Fluoropyridin-2-yl)-1H-pyrazol-4-yl]methyl}-1,3-oxazinan-3-yl][5-methyl-2-(2H-1,2,3-triazol-2-yl)phenyl]methanone

[Formula 52]

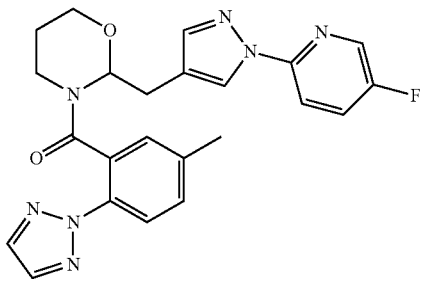

By using 2-[1-(5-fluoropyridin-2-yl)-1H-pyrazol-4-yl]ethanol obtained in Reference Example 22 (0.30 g, 1.5 mmol) as the raw material, the same procedure as in Reference Example 25 was carried out to obtain the racemic mixture of title compound (0.19 g) (colorless solid). The obtained racemic mixture was divided using a semi-preparative column based on the racemic compound analysis condition described earlier (condition 11, $Rt^1$=9.9 min, $Rt^2$=11.5 min) to obtain the title compound (0.0095 g) (colorless solid) having a short relative retention time ($Rt^1$=9.9 min).

LCMS retention time: 0.97 min.
MS (ESI pos.) m/z: 448 [M+H]$^+$
$[\alpha]_D^{23}$=−21.4 (c=0.109, CHCl$_3$)

Example 48

(−)-(2-{[3-(5-Fluoropyridin-2-yl)-1H-pyrazol-1-yl]methyl}-1,3-oxazinan-3-yl)[5-methyl-2-(2H-1,2,3-triazol-2-yl)phenyl]methanone

[Formula 53]

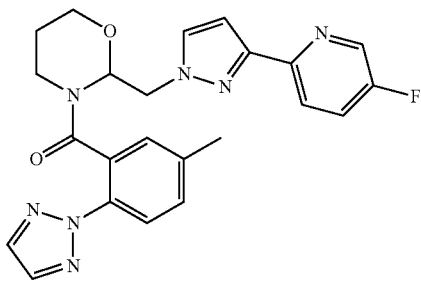 [SMILES: O=C(c1cc(F)ccc1-n1nccn1)N1CCCOC1Cn1ccc(-c2ccc(F)cn2)n1]

To a solution of 5-fluoro-2-(1H-pyrazol-3-yl)pyridine obtained in Reference Example 10 (0.36 g, 2.2 mmol) in DMF (9 mL), sodium hydride (55%, 0.12 g, 2.7 mmol) was added, and the resulting mixture was stirred for 30 minutes at room temperature. A solution of [2-(chloromethyl)-1,3-oxazinan-3-yl][5-methyl-2-(2H-1,2,3-triazol-2-yl)phenyl]methanone obtained in Reference Example 32 (0.79 g, 2.5 mmol, 84.2% ee) in DMF (3 mL) was added dropwise thereto. The reaction mixture was stirred for 1 hour at 90° C. The reaction mixture was allowed to cool to room temperature, then water was added thereto, followed by extraction with EtOAc.

The organic layer was washed with water and a saturated aqueous solution of sodium chloride, dried over Na$_2$SO$_4$, then the drying agent was filtered off, and then the solvent was distilled off under reduced pressure. The obtained residue was purified by column chromatography (HP-Sil 40 g, hexane/EtOAc=70/30 to 0/100). EtOH (10 mL) was added thereto, the resulting mixture was stirred for 1 hour under cooling in an ice bath and then filtered out to obtain the title compound (0.60 g, >99.9% ee, the same stereochemistry as in Example 3) (colorless solid). The optical purity was analyzed based on the racemic compound analysis conditions described earlier (condition 9, $Rt^1$=4.3 min, $Rt^2$=6.7 min) to obtain an excess of the compound having a short relative retention time ($Rt^1$=4.3 min).

LCMS retention time: 0.90 min.
MS (ESI pos.) m/z: 448 [M+H]$^+$

Example 49

(−)-[(2S*,5R*)-2-{[4-(5-Fluoropyridin-2-yl)-1H-pyrazol-1-yl]methyl}-5-methyl-1,3-oxazinan-3-yl][5-methyl-2-(2H-1,2,3-triazol-2-yl)phenyl]methanone

[Formula 54]

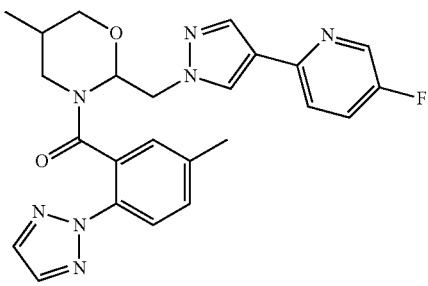

By using (2RS,5SR)-[2-(chloromethyl)-5-methyl-1,3-oxazinan-3-yl][5-methyl-2-(2H-1,2,3-triazol-2-yl)phenyl]methanone obtained in Reference Example 35 (0.52 g, 1.5 mmol) and 5-fluoro-2-(1H-pyrazol-4-yl)pyridine obtained in Reference Example 11 (0.23 g, 1.4 mmol), the same procedure as in Example 48 was carried out to obtain the title compound (0.44 g). The obtained racemic mixture (0.070 g) was divided using a semi-preparative column based on the racemic compound analysis condition described earlier (condition 13, $Rt^1$=6.6 min, $Rt^2$=12.4 min) to obtain the title compound (0.030 g) having a short relative retention time ($Rt^1$=6.6 min) (colorless oil).

LCMS retention time: 0.95 min.
MS (ESI pos.) m/z: 462 [M+H]$^+$
$[\alpha]_D^{25}$=−14.1 (c=0.0870, CHCl$_3$)

Test Example

Measurement of Orexin Antagonistic Activity

The antagonistic activities of the test compounds on human orexin-1 receptor (hOX1R) and orexin-2 receptor (hOX2R) were measured by modifying from the method described in literature (Toshikatsu Okumura et al., Biochemical and Biophysical Research Communications 280, 976-981, 2001). Chinese hamster ovary (CHO) cells forcibly expressing the hOX1R and hOX2R were seeded into a 96 well Black clear bottom plate (Nunc) at 20,000 cells per well, which were cultured in Ham's F-12 medium containing 0.1 mM MEM non-essential amino acids, 0.5 mg/ml G418, 10% fetal bovine serum (all by Invitrogen) for 16 hours under the conditions of 37° C., 5% CO2. After removing the medium, 100 μL of 0.5 μM Fluo-4AM ester (Dojin) in an assay buffer (25 mM HEPES (Dojin), Hank's balanced salt solution (Invitrogen), 0.1% bovine serum albumin, 2.5 mM probenecid, 200 μg/ml Amaranth (all by Sigma-Aldrich), pH 7.4) was added and the cells were incubated for 60 minutes at 37° C., 5% CO2. After removing the assay buffer containing fluo-3AM ester, the test compound was dissolved in dimethyl sulfoxide to be 10 mM and diluted with the assay buffer, 150 μL of which was added and incubated for 30 minutes.

The ligand peptide, in which 2 amino acids of human orexin-A are substituted (Pyr-Pro-Leu-Pro-Asp-Ala-Cys-Arg-Gln-Lys-Thr-Ala-Ser-Cys-Arg-Leu-Tyr-Glu-Leu-Leu-His-Gly-Ala-Gly-Asn-His-Ala-Ala-Gly-Ile-Leu-Thr-Leu-NH2; Peptide Institute, Inc.), were diluted with an assay buffer to give the final concentration of 300 pM for hOX1R and 3 nM for hOX2R, and 50 μL of the ligand solution was added to start the reaction. The reaction was measured for the fluorescence intensity of each well every second for 3 minutes using Functional Drug Screening System (FDSS; Hamamatsu Photonics K.K.), and the antagonistic activity was determined using the maximum fluorescence intensity as the indicator of intracellular Ca2+ concentration. The antagonistic activity of test compound was calculated when the fluorescence intensity of wells to which only the dilution buffer was added is 100% and the fluorescence intensity of wells to which the buffer containing no ligand or compound was added is 0%, and the 50% inhibition concentration ($IC_{50}$ value) was determined from the fluorescence intensities when the several concentrations of compounds were added.

The $IC_{50}$ values of the compounds of the present invention are shown in Table 6.

TABLE 6

| Example No. | $IC_{50}$ Value | |
|---|---|---|
| | OX1 (nM) | OX2 (nM) |
| 1 | 4.9 | 18.5 |
| 2 | 14.3 | 18.6 |
| 3 | 0.7 | 1.2 |
| 4 | 9.6 | 3.2 |
| 5 | 86.0 | 11.5 |
| 6 | 27.5 | 9.8 |
| 7 | 7.2 | 54.9 |
| 8 | 60.9 | 460.1 |
| 9 | 23.4 | 41.5 |
| 10 | 200.6 | 273.4 |
| 11 | 17.5 | 252.0 |
| 12 | 19.5 | 170.9 |
| 13 | 121.0 | 251.4 |
| 14 | 9.7 | 9.5 |
| 15 | 16.9 | 224.8 |
| 16 | 28.9 | 71.7 |
| 17 | 5.1 | 46.7 |
| 18 | 26.4 | 192.2 |
| 19 | 76.8 | 232.7 |
| 20 | 12.3 | 100.8 |
| 21 | 30.2 | 234.1 |
| 22 | 2.4 | 2.4 |
| 23 | 96.3 | 112.4 |
| 24 | 34.6 | 26.7 |
| 25 | 98.6 | 107.0 |
| 26 | 21.7 | 59.1 |

TABLE 6-continued

| Example No. | $IC_{50}$ Value | |
|---|---|---|
| | OX1 (nM) | OX2 (nM) |
| 27 | 0.9 | 3.0 |
| 28 | 2.4 | 4.0 |
| 29 | 3.2 | 1.2 |
| 30 | 2.6 | 3.0 |
| 31 | 10.9 | 7.3 |
| 32 | 34.4 | 22.6 |
| 33 | 3593.0 | 4544.3 |
| 34 | 2.2 | 6.2 |
| 35 | 0.8 | 1.0 |
| 36 | 3.8 | 6.9 |
| 37 | 1.1 | 1.7 |
| 38 | 2.1 | 7.3 |
| 39 | 81.2 | 46.6 |
| 40 | 8.3 | 1.4 |
| 41 | 1.0 | 1.0 |
| 42 | 17.2 | 20.4 |
| 43 | 2.6 | 3.2 |
| 44 | 60.4 | 51.8 |
| 45 | 2.7 | 12.1 |
| 46 | 31.9 | 38.7 |
| 47 | 3.4 | 3.6 |
| 49 | 0.8 | 7.7 |

INDUSTRIAL APPLICABILITY

The compounds of the present invention are verified to have the OX receptor antagonistic activities. Thus, the compounds of the present invention or the pharmaceutically acceptable salts thereof can be used as a therapeutic or preventive drug for diseases regulated by OX receptor antagonistic activities such as sleep disorder, depression, anxiety disorder, panic disorder, schizophrenia, drug dependence, Alzheimer's disease, Parkinson's disease, Huntington's disease, eating disorder, headache, migraine, pain, gastrointestinal disease, epilepsy, inflammation, immunological disease, endocrine disease and hypertension.

The invention claimed is:
1. A compound represented by formula (IA):

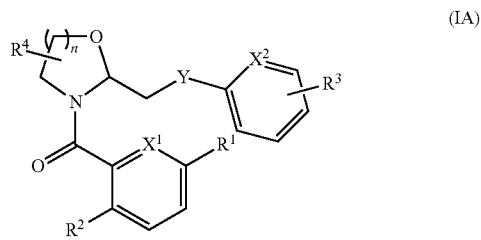

wherein,
$X^1$ and $X^2$ are the same or different and represent a nitrogen atom or formula CH;
Y represents any of the structures in the following formula group (a):

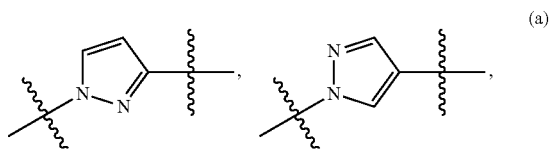

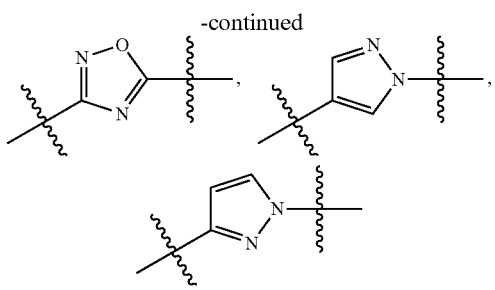

n represents 1 or 2;
R[1] represents a hydrogen atom, a halogen atom or a $C_{1-6}$ alkyl group;
R[2] represents a triazolyl group, a pyridyl group or a pyrimidinyl group;
R[3] represents a hydrogen atom, a halogen atom or a $C_{1-6}$ alkyl group, wherein the $C_{1-6}$ alkyl group may optionally be substituted with 1 to 3 halogen atoms; and
R[4] represents a hydrogen atom or a $C_{1-6}$ alkyl group;
or a pharmaceutically acceptable salt thereof.

2. The compound or a pharmaceutically acceptable salt thereof according to claim 1,
wherein, in the above formula (IA),
R[2] is a triazolyl group or a pyrimidinyl group; and
R[3] is a halogen atom.

3. The compound or a pharmaceutically acceptable salt thereof according to claim 1, wherein, in the above formula (IA), n is 2.

4. A compound represented by formula (I):

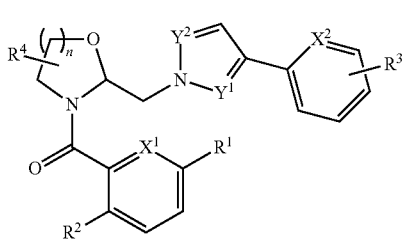

wherein,
X[1] and X[2] are the same or different and represent a nitrogen atom or formula CH;
either one of Y[1] and Y[2] represents a nitrogen atom, and the other represents CH;
n represents 1 or 2;
R[1] represents a hydrogen atom, a halogen atom or a $C_{1-6}$ alkyl group;
R[2] represents a triazolyl group, a pyridyl group or a pyrimidinyl group;
R[3] represents a hydrogen atom, a halogen atom or a $C_{1-6}$ alkyl group, wherein the $C_{1-6}$ alkyl group may optionally be substituted with 1 to 3 halogen atoms; and
R[4] represents a hydrogen atom or a $C_{1-6}$ alkyl group;
or a pharmaceutically acceptable salt thereof.

5. The compound or a pharmaceutically acceptable salt thereof according to claim 4,
wherein, in the above formula (I),
R[2] is a triazolyl group or a pyrimidinyl group; and
R[3] is a halogen atom.

6. The compound or a pharmaceutically acceptable salt thereof according to claim 4, wherein, in the above formula (I), n is 2.

7. The compound or a pharmaceutically acceptable salt thereof according to claim 1, which is a species or a mixture of two or more species selected from:

(−)-(2-{[3-(5-fluoropyridin-2-yl)-1H-pyrazol-1-yl]methyl}-1,3-oxazolidin-3-yl)[5-methyl-2-(2H-1,2,3-triazol-2-yl)phenyl]methanone, (−)-(2-{[4-(5-fluoropyridin-2-yl)-1H-pyrazol-1-yl]methyl}-1,3-oxazolidin-3-yl)[5-methyl-2-(2H-1,2,3-triazol-2-yl)phenyl]methanone, (−)-(2-{[3-(5-fluoropyridin-2-yl)-1H-pyrazol-1-yl]methyl}-1,3-oxazinan-3-yl)[5-methyl-2-(2H-1,2,3-triazol-2-yl)phenyl]methanone, (−)-(2-{[4-(5-fluoropyridin-2-yl)-1H-pyrazol-1-yl]methyl}-1,3-oxazinan-3-yl)[5-methyl-2-(2H-1,2,3-triazol-2-yl)phenyl]methanone, (−)-[(2S,5S)-2-{[4-(5-fluoropyridin-2-yl)-1H-pyrazol-1-yl]methyl}-5-methyl-1,3-oxazolidin-3-yl][5-methyl-2-(2H-1,2,3-triazol-2-yl)phenyl]methanone, (−)-[(2S,5R)-2-{[4-(5-fluoropyridin-2-yl)-1H-pyrazol-1-yl]methyl}-5-methyl-1,3-oxazolidin-3-yl][5-methyl-2-(2H-1,2,3-triazol-2-yl)phenyl]methanone,

[(2S,4R)-2-{[3-(5-fluoropyridin-2-yl)-1H-pyrazol-1-yl]methyl}-4-methyl-1,3-oxazolidin-3-yl][5-methyl-2-(2H-1,2,3-triazol-2-yl)phenyl]methanone, (−)-[(2S,4S)-2-{[3-(5-fluoropyridin-2-yl)-1H-pyrazol-1-yl]methyl}-4-methyl-1,3-oxazolidin-3-yl][5-methyl-2-(2H-1,2,3-triazol-2-yl)phenyl]methanone, (±)-2-{[3-(5-fluoropyridin-2-yl)-1H-pyrazol-1-yl]methyl}-1,3-oxazolidin-3-yl][5-methyl-2-(pyrimidin-2-yl)phenyl]methanone, (±)-(2-{[3-(5-fluoropyridin-2-yl)-1H-pyrazol-1-yl]methyl}-1,3-oxazolidin-3-yl)[5-fluoro-2-(pyrimidin-2-yl)phenyl]methanone, (±)-(2-{[3-(4-fluorophenyl)-1H-pyrazol-1-yl]methyl}-1,3-oxazolidin-3-yl)[5-methyl-2-(2H-1,2,3-triazol-2-yl)phenyl]methanone, (±)-(2-{[4-(4-fluorophenyl)-1H-pyrazol-1-yl]methyl}-1,3-oxazolidin-3-yl)[5-methyl-2-(2H-1,2,3-triazol-2-yl)phenyl]methanone, (±)-(2-{[4-(4-fluorophenyl)-1H-pyrazol-1-yl]methyl}-1,3-oxazolidin-3-yl)[5-methyl-2-(pyrimidin-2-yl)phenyl]methanone, (−)-(2-{[3-(4-fluorophenyl)-1H-pyrazol-1-yl]methyl}-1,3-oxazolidin-3-yl)[6-methyl-3-(2H-1,2,3-triazol-2-yl)pyridin-2-yl]methanone, (−)-(2-{[3-(4-fluorophenyl)-1H-pyrazol-1-yl]methyl}-1,3-oxazinan-3-yl)[6-methyl-3-(2H-1,2,3-triazol-2-yl)pyridin-2-yl]methanone, (−)-(2-{[3-(4-fluorophenyl)-1H-pyrazol-1-yl]methyl}-1,3-oxazinan-3-yl)[6-methyl-3-(pyrimidin-2-yl)pyridin-2-yl]methanone, (−)-(2-{[3-(5-fluoropyridin-2-yl)-1H-pyrazol-1-yl]methyl}-1,3-oxazinan-3-yl)[5-fluoro-2-(2H-1,2,3-triazol-2-yl)phenyl]methanone, (−)-(2-{[3-(5-fluoropyridin-2-yl)-1H-pyrazol-1-yl]methyl}-1,3-oxazinan-3-yl)[5-methyl-2-(pyrimidin-2-yl)phenyl]methanone, (−)-(2-{[4-(4-fluorophenyl)-1H-pyrazol-1-yl]methyl}-1,3-oxazinan-3-yl)[6-methyl-3-(2H-1,2,3-triazol-2-yl)pyridin-2-yl]methanone, (−)-(2-{[4-(4-fluorophenyl)-1H-pyrazol-1-yl]methyl}-1,3-oxazinan-3-yl)[6-methyl-3-(pyrimidin-2-yl)pyridin-2-yl]methanone, (−)-[2-{[3-(5-fluoropyridin-2-yl)-1H-pyrazol-1-yl]methyl}-1,3-oxazinan-3-yl][5-fluoro-2-(pyrimidin-2-yl)phenyl]methanone, (−)-[2-{[4-(4-fluorophenyl)-1H-pyrazol-1-yl]methyl}-1,3-oxazinan-3-yl][5-methyl-2-(2H-1,2,3-triazol-2-yl)phenyl]methanone,
(−)-[2-{[5-(5-fluoropyridin-2-yl)-1,2,4-oxadiazol-3-yl]methyl}-1,3-oxazinan-3-yl][5-methyl-2-(2H-1,2,3-triazol-2-yl)phenyl]methanone,
(−)-[2-{[5-(4-fluorophenyl)-1,2,4-oxadiazol-3-yl]methyl}-1,3-oxazinan-3-yl][5-methyl-2-(2H-1,2,3-triazol-2-yl)phenyl]methanone,
(−)-[2-{[5-(4-fluorophenyl)-1,2,4-oxadiazol-3-yl]methyl}-1,3-oxazinan-3-yl][6-methyl-3-(2H-1,2,3-triazol-2-yl)pyridin-2-yl]methanone,
[(2S,4S)-2-{[4-(5-fluoropyridin-2-yl)-1H-pyrazol-1-yl]methyl}-4-methyl-1,3-oxazinan-3-yl][5-methyl-2-(2H-1,2,3-triazol-2-yl)phenyl]methanone,
(−)-[(2S*,5S*)-2-{[4-(5-fluoropyridin-2-yl)-1H-pyrazol-1-yl]methyl}-5-methyl-1,3-oxazinan-3-yl][5-methyl-2-(2H-1,2,3-triazol-2-yl)phenyl]methanone,
(−)-[2-{[3-(4-fluorophenyl)-1H-pyrazol-1-yl]methyl}-1,3-oxazinan-3-yl][5-methyl-2-(pyrimidin-2-yl)phenyl]methanone,
(±)-[2-{[1-(5-fluoropyridin-2-yl)-1H-pyrazol-4-yl]methyl}-1,3-oxazinan-3-yl][5-methyl-2-(pyrimidin-2-yl)phenyl]methanone,
(−)-[2-{[4-(4-fluorophenyl)-1H-pyrazol-1-yl]methyl}-1,3-oxazinan-3-yl][5-methyl-2-(pyrimidin-2-yl)phenyl]methanone,
(−)-[2-{[1-(5-fluoropyridin-2-yl)-1H-pyrazol-4-yl]methyl}-1,3-oxazinan-3-yl][5-fluoro-2-(pyrimidin-2-yl)phenyl]methanone,
(−)-[2-{[1-(5-fluoropyridin-2-yl)-1H-pyrazol-3-yl]methyl}-1,3-oxazolidin-3-yl][5-methyl-2-(2H-1,2,3-triazol-2-yl)phenyl]methanone,
(−)-[2-{[1-(5-fluoropyridin-2-yl)-1H-pyrazol-4-yl]methyl}-1,3-oxazolidin-3-yl][5-methyl-2-(2H-1,2,3-triazol-2-yl)phenyl]methanone,
(−)-[2-{[1-(5-fluoropyridin-2-yl)-1H-pyrazol-4-yl]methyl}-1,3-oxazinan-3-yl][5-methyl-2-(2H-1,2,3-triazol-2-yl)phenyl]methanone,
(−)-[(2S*,5R*)-2-{[4-(5-fluoropyridin-2-yl)-1H-pyrazol-1-yl]methyl}-5-methyl-1,3-oxazinan-3-yl][5-methyl-2-(2H-1,2,3-triazol-2-yl)phenyl]methanone.

8. A pharmaceutical composition containing the compound or a pharmaceutically acceptable salt thereof according to claim 1, as an active ingredient and a pharmaceutically acceptable carrier.

9. A method for treating insomnia, depression, anxiety disorder, panic disorder, drug dependence, eating disorder, headache, migraine, comprising administering to a subject in need of treatment an effective amount of the compound or a pharmaceutically acceptable salt thereof according to claim 1, as an active ingredient.

* * * * *